US012146171B2

(12) United States Patent
Treier-Marxen et al.

(10) Patent No.: US 12,146,171 B2
(45) Date of Patent: Nov. 19, 2024

(54) METHOD OF RECOVERING A PROTEIN FROM FERMENTATION BROTH USING A DIVALENT CATION

(71) Applicant: BASF SE, Ludwigshafen (DE)

(72) Inventors: Katrin Treier-Marxen, Ludwigshafen (DE); Sebastian Schoof, Ludwigshafen (DE); Andreas Schaedler, Weyher (DE); Stephan Freyer, Ludwigshafen (DE); Michael Helmut Kopf, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 417 days.

(21) Appl. No.: 17/615,160

(22) PCT Filed: Jun. 9, 2020

(86) PCT No.: PCT/EP2020/065929
§ 371 (c)(1),
(2) Date: Nov. 30, 2021

(87) PCT Pub. No.: WO2020/249546
PCT Pub. Date: Dec. 17, 2020

(65) Prior Publication Data
US 2022/0275355 A1    Sep. 1, 2022

(30) Foreign Application Priority Data

Jun. 13, 2019  (EP) .................................. 19180081

(51) Int. Cl.
| | |
|---|---|
| C12N 9/00 | (2006.01) |
| C07K 1/14 | (2006.01) |
| C12N 1/20 | (2006.01) |
| C12N 9/28 | (2006.01) |
| C12R 1/10 | (2006.01) |

(52) U.S. Cl.
CPC .............. C12N 9/2417 (2013.01); C07K 1/14 (2013.01); C12N 1/20 (2013.01); C12Y 302/01001 (2013.01); C12R 2001/10 (2021.05)

(58) Field of Classification Search
CPC .......... C12N 9/2417; C12N 1/20; C12N 9/00; C07K 1/14; C07K 1/145; C12Y 302/01001; C12R 2001/10
See application file for complete search history.

(56) References Cited

U.S. PATENT DOCUMENTS

| | | | |
|---|---|---|---|
| 3,451,935 | A | 6/1969 | Roald et al. |
| 6,124,127 | A | 9/2000 | Andersen et al. |
| 6,316,240 | B1 | 11/2001 | Laustsen et al. |
| 7,118,891 | B2 | 10/2006 | Nielsen et al. |
| 2002/0177206 | A1 | 11/2002 | Heng |
| 2011/0089344 | A1 | 4/2011 | Fujimura et al. |
| 2012/0220009 | A1 | 8/2012 | Bodo et al. |

FOREIGN PATENT DOCUMENTS

| | | |
|---|---|---|
| DE | 10064983 A1 | 7/2002 |
| DE | 10304331 A1 | 8/2004 |
| DE | 102005028295 A1 | 11/2006 |
| EP | 0283075 A2 | 9/1988 |
| EP | 1921147 A2 | 5/2008 |
| GB | 1300596 A | 12/1972 |
| WO | WO-89/06279 A1 | 7/1989 |
| WO | WO-91/02792 A1 | 3/1991 |
| WO | WO-92/19729 A1 | 11/1992 |
| WO | WO-94/02597 A1 | 2/1994 |
| WO | WO-94/18314 A1 | 8/1994 |
| WO | WO-94/19444 A1 | 9/1994 |
| WO | WO-95/10603 A1 | 4/1995 |
| WO | WO-95/23221 A1 | 8/1995 |
| WO | WO-95/26397 A1 | 10/1995 |
| WO | WO-96/23872 A1 | 8/1996 |
| WO | WO-96/23873 A1 | 8/1996 |
| WO | WO-96/23874 A1 | 8/1996 |
| WO | WO-96/34946 A1 | 11/1996 |
| WO | WO-96/38469 A1 | 12/1996 |
| WO | WO-97/25417 A1 | 7/1997 |
| WO | WO-97/43424 A1 | 11/1997 |
| WO | WO-97/43482 A1 | 11/1997 |
| WO | WO-98/20115 A1 | 5/1998 |
| WO | WO-98/20116 A1 | 5/1998 |
| WO | WO-98/24799 A1 | 6/1998 |
| WO | WO-98/37179 A2 | 8/1998 |
| WO | WO-99/11768 A1 | 3/1999 |
| WO | WO-99/19467 A1 | 4/1999 |
| WO | WO-99/27083 A1 | 6/1999 |
| WO | WO-99/27084 A1 | 6/1999 |
| WO | WO-99/64619 A2 | 12/1999 |
| WO | WO-00/22103 A1 | 4/2000 |
| WO | WO-00/32758 A1 | 6/2000 |
| WO | WO-00/43502 A1 | 7/2000 |
| WO | WO-00/60060 A2 | 10/2000 |
| WO | WO-01/44452 A1 | 6/2001 |

(Continued)

OTHER PUBLICATIONS

Delmar, et al., "A sensitive new substrate for chymotrypsin1", Analytical Biochemistry, vol. 99, Issue 2, Nov. 1, 1979, pp. 316-320.
European Search Report for EP Patent Application No. 19180081.2, Issued on Jan. 9, 2020, 3 pages.
Gupta, et al., "An overview on fermentation, downstream processing and properties of microbial alkaline proteases", Applied Microbiology and Biotechnology, vol. 60, Issue 4, Dec. 2002, pp. 381-395.
Hoffman, "A rapid photoelectric method for the determination of glucose in blood and urine", Journal of Biological Chemistry, vol. 120, Issue 1, 1937, pp. 51-55.

(Continued)

*Primary Examiner* — Satyendra K Singh
(74) *Attorney, Agent, or Firm* — ArentFox Schiff LLP

(57) ABSTRACT

The present invention relates to a method for recovering a protein of interest from a fermentation broth by adding a salt of a divalent cation and increasing the pH.

13 Claims, 3 Drawing Sheets

(56) References Cited

FOREIGN PATENT DOCUMENTS

| | | |
|---|---|---|
| WO | WO-01/66712 A2 | 9/2001 |
| WO | WO-02/06442 A2 | 1/2002 |
| WO | WO-02/10355 A2 | 2/2002 |
| WO | WO-02/068589 A2 | 9/2002 |
| WO | WO-02/068597 A2 | 9/2002 |
| WO | WO-02/088340 A2 | 11/2002 |
| WO | WO-02/092741 A2 | 11/2002 |
| WO | WO-03/006602 A2 | 1/2003 |
| WO | WO-03/054184 A1 | 7/2003 |
| WO | WO-03/055974 A2 | 7/2003 |
| WO | WO-03/056017 A2 | 7/2003 |
| WO | WO-03/068910 A2 | 8/2003 |
| WO | WO-03/83054 A2 | 10/2003 |
| WO | WO-03/089620 A2 | 10/2003 |
| WO | WO-03/095638 A1 | 11/2003 |
| WO | WO-2004/003187 A2 | 1/2004 |
| WO | WO-2004/003216 A2 | 1/2004 |
| WO | WO-2004/041979 A2 | 5/2004 |
| WO | WO-2004/090099 A2 | 10/2004 |
| WO | WO-2004/091544 A2 | 10/2004 |
| WO | WO-2005/003319 A2 | 1/2005 |
| WO | WO-2005/032496 A2 | 4/2005 |
| WO | WO-2005/063974 A1 | 7/2005 |
| WO | WO-2005/086900 A2 | 9/2005 |
| WO | WO-2005/103244 A1 | 11/2005 |
| WO | WO-2006/000976 A1 | 1/2006 |
| WO | WO-2006/002643 A2 | 1/2006 |
| WO | WO-2006/031699 A2 | 3/2006 |
| WO | WO-2006/066594 A2 | 6/2006 |
| WO | WO-2007/006305 A1 | 1/2007 |
| WO | WO-2008/036863 A2 | 3/2008 |
| WO | WO-2008/080093 A2 | 7/2008 |
| WO | WO-2008/110498 A1 | 9/2008 |
| WO | WO-2009/020459 A2 | 2/2009 |
| WO | WO-2009/061380 A2 | 5/2009 |
| WO | WO-2010/104675 A1 | 9/2010 |
| WO | WO-2011/003784 A1 | 1/2011 |
| WO | WO-2011/036263 A1 | 3/2011 |
| WO | WO-2011/036264 A1 | 3/2011 |
| WO | WO-2011/046812 A1 | 4/2011 |
| WO | WO-2011/072099 A2 | 6/2011 |
| WO | WO-2011/098531 A1 | 8/2011 |
| WO | WO-2013/001078 A1 | 1/2013 |
| WO | WO-2013/001087 A2 | 1/2013 |
| WO | WO-2013/184577 A1 | 12/2013 |
| WO | WO-2014/059360 A1 | 4/2014 |
| WO | WO-2015/155350 A1 | 10/2015 |
| WO | WO-2015/155351 A1 | 10/2015 |
| WO | WO-2015/166075 A1 | 11/2015 |
| WO | WO-2015/181286 A1 | 12/2015 |
| WO | WO-2015/181287 A1 | 12/2015 |
| WO | WO-2016/096711 A2 | 6/2016 |
| WO | WO-2017/068012 A1 | 4/2017 |
| WO | WO-2017/097869 A1 | 6/2017 |

OTHER PUBLICATIONS

Jacobs, et al., "Cloning, sequencing and expression of subtilisin Carlsberg from Bacillus licheniformis", Nucleic Acids Research, vol. 13, Issue 24, Dec. 20, 1985, pp. 8913-8926.

Lorentz, "Routine ?-Amylase Assay Using Protected 4-Nitrophenyl-1,4-?-D-maltoheptaoside and a Novel ?-Glucosidase", Clinical Chemistry, vol. 46, Issue 5, May 1, 2000, pp. 644-649.

Needleman, et al., "A general method applicable to the search for similarities in the amino acid sequence of two proteins", Journal of Molecular Biology, vol. 48, Issue 3, Mar. 28, 1970, pp. 443-453.

Siezen, "Substilases: Subtilisin-like Serine Proteases", Subtilisin Enzymes—Practical Protein Engineering, ed. Bott, et al., 1996, pp. 75-93.

Siezen, et al., "Homology modelling and protein engineering strategy of subtilases, the family of subtilisin-like serine proteinases", Protein Engineering, Design and Selection, vol. 4, Issue 7, Oct. 1, 1991, pp. 719-737.

Siezen, et al., "Subtilases: the superfamily of subtilisin-like serine proteases", Protein Sciences, vol. 6, Issue 3, Mar. 1997, pp. 501-523.

Smith, et al., "Subtilisin Carlsberg: V. The complete sequence; comparison with subtilisin BPN?; evolutionary relationships", Journal of Biological Chemistry, vol. 243, Issue 9, May 1968, pp. 2184-2191.

Vasantha, et al., "Genes for alkaline protease and neutral protease from Bacillus amyloliquefaciens contain a large open reading frame between the regions coding for signal sequence and mature protein", Journal of Bacteriology, vol. 159, Issue 3, 1984, pp. 811-819.

Wells, et al., "Cloning, sequencing, and secretion of Bacillus amyloliquefaciens subtillisin in Bacillus subtilis", Nucleic Acids Research, vol. 11, Issue 22, Nov. 25, 1983, pp. 7911-7925.

International Application No. PCT/EP2020/065929, International Search Report and Written Opinion, mailed Jul. 13, 2020.

International Application No. PCT/EP2020/065929, International Preliminary Report on Patentability, mailed Nov. 9, 2021.

METHOD OF RECOVERING A PROTEIN FROM FERMENTATION BROTH USING A DIVALENT CATION

CROSS-REFERENCE TO RELATED APPLICATIONS

This is the U.S. national phase of International Application No. PCT/EP2020/065929, filed Jun. 9, 2020, which claims the benefit of European Patent Application No. 19180081.2, filed on Jun. 13, 2019.

FIELD OF THE INVENTION

The present invention relates to a method for recovering a protein of interest from a culture broth by adding a divalent cation and increasing the pH.

BACKGROUND OF THE INVENTION

In the synthesis step of industrial proteins like enzymes, the fermentation step, high titers are achieved. These high protein concentrations can lead to a partial phase transfer from the solubilized to insolubilized state in the culture broth. It is possible that the protein is present in form of crystals, precipitates and/or is adsorbed on the solids of the fermentation broth. Partially solubilized and insolubilized protein complicates separation of the protein from the solids in the culture broth and can lead to loss of product. The increase of manufacturing costs due to loss of product or due to a more complicated separation process determines if product loss is tolerated or product concentration in one phase is increased by additional process steps. Therefore, methods were established to increase the percentage of protein in the liquid or in the solid phase.

Several patent applications are directed to an increased solubility of enzymes or proteins in the fermentation broth: WO 2004/003187 describes the approach of preventing crystallization by addition of polyols, carbohydrates or polyethers. Other patent applications describe methods to increase the percentage of insoluble enzyme and/or to influence crystal morphology to simplify the following solid-liquid separation: US 2002/177206 presents a crystallization process to attain desirable crystal morphology and size. In this method a starting temperature is selected to attain a desirable crystal morphology and then a temperature shift is introduced. At this temperature, the crystals continue to grow in desirable fashion with a higher rate of crystallization and further nucleation is prevented. US 2011/89344 presents different methods to increase the percentage of insoluble enzyme in a fermentation broth.

Other patent applications describe how the fermentation broth conditions are changed during solid-liquid separation: In US 2012/220009 two different broth conditions are applied. First, the protein of interest is retained by a membrane and after a change of conditions broth permeates through the same or another membrane. The first set of conditions can also cause precipitation or crystallization. In other documents special apparatuses are used to separate the two solid phases, biomass and solid enzyme: U.S. Pat. No. 7,118,891 describes a method in which a fermentation broth is treated with one or more coagulants and/or one or more flocculants to form biomass flocks without incorporating the crystalline and/or amorphous metabolites in the flocks. Then the flocculated biomass is separated from the crystalline and/or amorphous metabolite suspension using a solid liquid separation apparatus like a two-phase centrifuge.

In U.S. Pat. No. 6,316,240 enzymes are solubilized before biomass separation by adjusting the pH between 9.5 and 13. WO 2008/110498 describes a method to solubilize protease crystals or precipitates in fermentation broth by diluting the broth, adding a divalent salt, and adjusting the pH value of the fermentation broth to a pH value below pH 5.5. WO 2017/097869 proposes a method to solubilize and/or desorb a protein of interest from particulate matters of the fermentation broth by applying one or more wash steps where pH and conductivity of the wash solution are adapted in dependency of the protein's pI.

However, an alkaline or acidic pH treatment during recovery of the protein may lead to loss of protein activity. Therefore, a novel method for recovering a protein of interest from a fermentation broth is needed which aims at high product yield and preserves the activity of the protein.

SUMMARY OF THE INVENTION

The present inventors have found that the addition of a divalent cation to a fermentation broth comprising the protein of interest and adjustment of the pH of the fermentation broth to a pH above 11 leads to a high recovery rate and high remaining activity of the protein of interest.

Therefore, in a first aspect the invention relates to a method of recovering a protein of interest from a fermentation broth comprising the steps of
 a) adding a salt of a divalent cation to the fermentation broth or a fraction thereof comprising the protein of interest, and
 b) adjusting the pH of the fermentation broth to more than pH 11, and
 c) separating the protein of interest from impurities and/or biomass.

In an embodiment, the protein of interest is an enzyme.

The enzyme may be selected from the group consisting of amylase, alpha-amylase, glucoamylase, pullulanase, protease, metalloprotease, peptidase, lipase, cutinase, acyl transferase, cellulase, endoglucanase, glucosidase, cellobiohydrolase, xylanase, xyloglucantransferase, xylosidase, mannanase, phytase, phosphatase, xylose isomerase, glucoase isomerase, lactase, acetolactate decarboxylase, pectinase, pectin methylesterase, polygalacturonidase, lyase, pectate lyase, arabinase, arabinofuranosidase, galactanase, a laccase, peroxidase and an asparaginase, preferably wherein the enzyme is an amylase or protease.

In another embodiment, the divalent cation is selected from the group consisting of $Ca^{2+}$, $Mg^{2+}$, $Ba^{2+}$, $Pb^{2+}$, $Fe^{2+}$, $Zn^{2+}$, $Ni^{2+}$, $Mn^{2+}$, $Sr^{2+}$, $Co^{2+}$ and $Be^{2+}$.

In another embodiment, the salt of the divalent cation is the chloride, nitrate, formate, acetate, phosphate or sulfate salt of the divalent cation.

In an embodiment, step a) and step b) are performed simultaneously, or step a) is performed before step b).

In an embodiment, the pH is adjusted to a pH of between 11 and 13, preferably wherein the pH may be adjusted by adding NaOH.

In yet another embodiment, the method further comprises prior to step a) and/or b) the fermentation of a microorganism.

In another embodiment, the protein of interest is secreted by the microorganism into the fermentation broth. The microorganism may be a bacterium. The bacterium may be selected from the group consisting of *Bacillus, Streptomyces, Escherichia, Buttiauxella* and *Pseudomonas*. Alternatively, the microorganism may be a fungal cell selected from the phyla Ascomycota, Basidiomycota, Chytridiomycota, Zygomycota, and Oomycota, as well as all mitosporic fungi and Saccharomycoideae. Preferably, the fungal cell is selected from the group consisting of *Aspergillus, Penicillium, Candida, Trichoderma, Thermothelomyces*, in particular *Thermothelomyces* thermophile, and *Pichia*.

In an embodiment, the salt of the divalent cation is added to the fermentation broth to obtain a final concentration of 0.01-5% (w/v) of the salt of the divalent cation in the broth.

In an embodiment, the fermentation broth prior to the addition of the divalent cation comprises phosphate.

In a further embodiment, the method further comprises a step (d) of preparing a formulation containing the protein.

In a second aspect, the invention relates to a method of stabilizing a protein of interest in a fermentation broth or fraction thereof, said method comprising the steps of
a) adding a salt of a divalent cation to the fermentation broth comprising the protein of interest, and
b) adjusting the pH of the fermentation broth to a pH of more than 11.

Definitions

Figure 1:
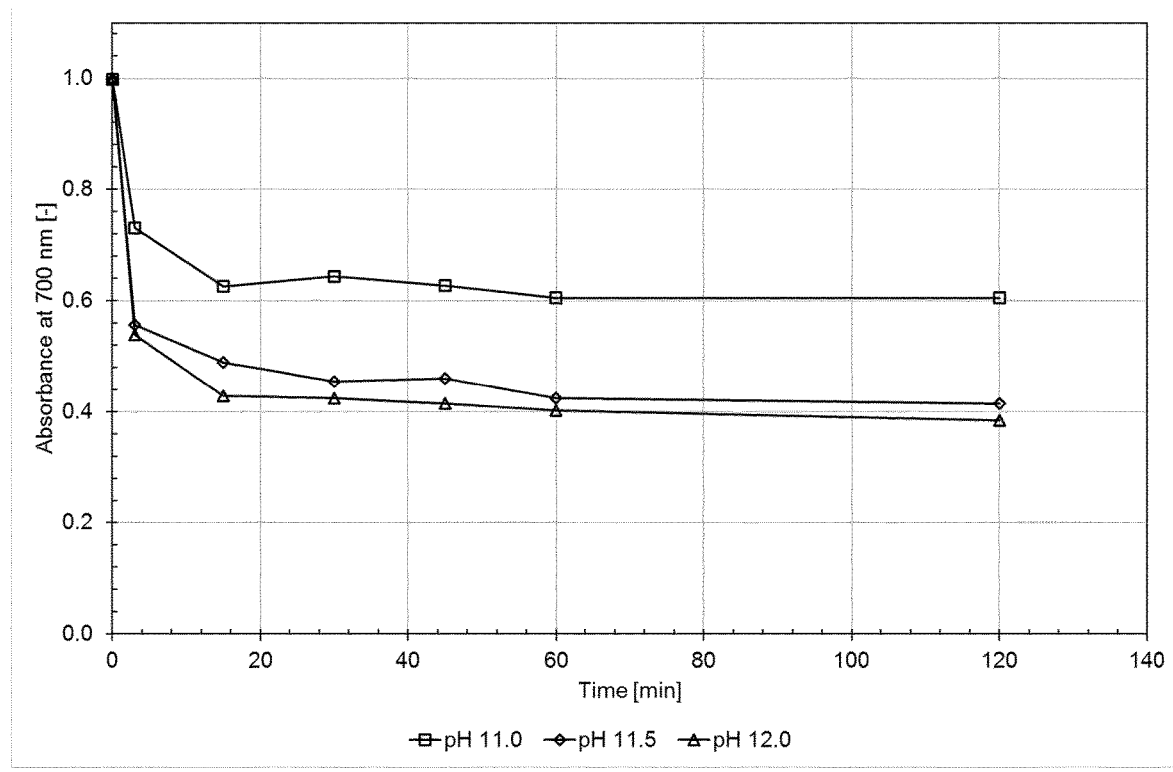
FIG. 1: Solubilization of the protein as measured by absorbance at 700 nm dependent on the pH of the supernatant.

Unless otherwise noted, the terms used herein are to be understood according to conventional usage by those of ordinary skill in the relevant art.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay, there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

Throughout this application, various publications are referenced. The disclosures of all of these publications and those references cited within those publications in their entireties are hereby incorporated by reference into this application in order to more fully describe the state of the art to which this invention pertains.

A "fermentation process" comprises the cultivation of cells in a suitable fermentation medium.

"Cultivation of the cells" or "growth of the cells" is not understood to be limited to an exponential growth phase, but can also include the physiological state of the cells at the beginning of growth after inoculation and during a stationary phase.

An industrially relevant fermentation process encompasses a fermentation process on a volume scale which is at least 1 m3 with regard to the nominal fermenter size, preferably at least 5 m3, more preferably at least 10 m3, even more preferably at least 25 m3, most preferably at least 50 m3. Preferably, the industrially relevant fermentation process encompasses a fermentation process on a volume scale which is 1-500 m3 with regard to the nominal fermenter size, preferably 5-500 m3, more preferably 10-500 m3, even more preferably 25-500 m3, most preferably 50-500 m3. In other words, an industrially relevant fermentation process encompasses a fermentation process on a volume scale which is at least 1000 L with regard to the nominal fermenter size, preferably at least 5,000 L, more preferably at least 10,000 L, even more preferably at least 25,000 L and most preferably at least 50,000 L. Preferably, the industrially relevant fermentation process encompasses a fermentation process on a volume scale which is 1000-500,000 L, preferably 5,000-500,000 L, more preferably 10,000-500,000 L, even more preferably 25,000-500,000 L and most preferably 50,000-500,000 L.

The term "fermentation broth" or "culture broth" as used herein describes the fermentation medium containing recombinant or non-recombinant cells, which are cultivated to express the protein of interest. In some embodiments, the recombinant or non-recombinant cells may secrete the protein of interest into the fermentation medium.

The term "fraction of the fermentation broth" denotes only part of the fermentation broth. Fractions of the fermentation broth may be obtained by centrifugation of the fermentation broth leading to a supernatant comprising the liquid part and a spin-down fraction comprising the cells and other insolubles. Alternatively, the fractions of the fermentation broth may be obtained by filtration of the fermentation broth leading to a filtrate or permeate comprising the liquid part and a retentate comprising the cells and/or other insolubles. Fractions may also include parts of the fermentation broth, if not the complete fermentation broth present in the fermenter is harvested for the recovery of the protein of interest.

The term "fermentation medium" refers to a water-based solution containing one or more chemical compounds that can support the growth of cells.

As used in this application, the term "divalent cation" means a cation having a +2 charge. Suitable divalent cations include $Ca^{2+}$, $Mg^{2+}$, $Ba^{2+}$, $Pb^{2+}$, $Fe^{2+}$, $Zn^{2+}$, $Ni^{2+}$, $Cu^{2+}$, $Mn^{2+}$, $Sr^{2+}$, $Co^{2+}$ and $Be^{2+}$. Preferably, the divalent cation is $Ca^{2+}$ or $Mg^{2+}$. The divalent cation can be in either solid or dissolved form, or both. In solid form, the cation is ionically bonded to an anion thereby making a salt, herein called "salt of a divalent cation" or "divalent salt".

"Impurities" in fermentation broth typically include unconverted sugars, residual salts and by-products.

The term "biomass" refers to cells which produce the desired product and fragments of these cells present in the fermentation broth.

The term "titer of a protein of interest" as used herein is understood as the amount of protein of interest in g per volume of fermentation broth in liter.

The terms "recovering" or "purifying" may be used interchangeably and are intended to mean "rendering more pure". They refer to a process in which the protein of interest is separated from other compounds or cells present in the fermentation broth.

The term "heterologous" (or exogenous or foreign or recombinant or non-native) polypeptide is defined herein as a polypeptide that is not native to the host cell, a polypeptide native to the host cell in which structural modifications, e.g., deletions, substitutions, and/or insertions, have been made by recombinant DNA techniques to alter the native polypeptide, or a polypeptide native to the host cell whose expression is quantitatively altered or whose expression is directed from a genomic location different from the native host cell as a result of manipulation of the DNA of the host cell by recombinant DNA techniques, or whose expression is quantitatively altered as a result of manipulation of the regulatory elements of the polynucleotide by recombinant DNA techniques e.g., a stronger promoter; or a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences are naturally not occurring in the specific combination with each other.

For the purposes of the invention, "recombinant" (or transgenic) with regard to a cell or an organism means that the cell or organism contains a heterologous polynucleotide which is introduced by man by gene technology and with regard to a polynucleotide includes all those constructions brought about by man by gene technology/recombinant DNA techniques in which either
  (a) the sequence of the polynucleotide or a part thereof, or
  (b) one or more genetic control sequences which are operably linked with the polynucleotide, including but not limited thereto a promoter, or
  (c) both a) and b)
are not located in their wildtype genetic environment or have been modified.

The term "native" (or wildtype or endogenous) cell or organism and "native" (or wildtype or endogenous) polynucleotide or polypeptide refers to the cell or organism as found in nature and to the polynucleotide or polypeptide in question as found in a cell in its natural form and genetic environment, respectively (i.e., without there being any human intervention).

The term "host cell", as used herein, includes any cell type that is susceptible to transformation, transfection, transduction, conjugation, and the like with a nucleic acid construct or expression vector.

The term "introduction" and variations thereof are defined herein as the transfer of a DNA into a host cell. The introduction of a DNA into a host cell can be accomplished by any method known in the art, including, the not limited to, transformation, transfection, transduction, conjugation, and the like.

DETAILED DESCRIPTION

The present invention may be understood more readily by reference to the following detailed description of the preferred embodiments of the invention and the examples included herein.

The inventors surprisingly found that the activity of a protein, e.g. an enzyme, can be retained or substantially retained, if a salt of a divalent cation is added to the fermentation broth before the pH is adjusted to pH values above pH 11.

An increase in pH to a value above 11 mediates the solubilization of the protein of interest which may be present in form of protein crystals, protein precipitates, and/or protein bound to the cell mass or other insoluble material (see Example 1). The high pH, however, may lead to a loss of protein activity of the protein of interest, e.g. an enzyme. Further, the high pH may lead to instability of the protein of interest, e.g. an enzyme.

Without wishing to be bound to a particular theory, it is hypothesized that phosphate ions present in the fermentation medium tend to extract divalent cations, preferably Ca2+, from the proteins, in particular enzymes, and to form insoluble salts, when the pH of the broth or fraction thereof is increased. By the addition of divalent cations to the fermentation broth before or simultaneous to increasing the pH, the phosphate in the medium complexes with these added cations and the cations bound to the enzyme will not be extracted. Therefore, the enzyme remains stable and soluble with reduced loss in its activity during the incubation at high pH.

Examples of suitable divalent cations that may be added to the fermentation broth include Group HA elements (alkaline earth metals). Particularly preferred divalent cations are Ca2+ and Mg2+.

Therefore, the invention relates to a method of recovering a protein of interest from a fermentation broth comprising the steps of
  a) adding a salt of a divalent cation to the fermentation broth or a fraction thereof comprising the protein of interest, and
  b) adjusting the pH of the fermentation broth to more than pH 11, and
  c) separating the protein of interest from impurities and/or biomass.

Furthermore, the invention relates to a method of stabilizing a protein of interest in a fermentation broth or fraction thereof, said method comprising the steps of
  a) adding a salt of a divalent cation to the fermentation broth comprising the protein of interest, and
  b) adjusting the pH of the fermentation broth to a pH of more than 11.

The method of the invention may be applied to the fermentation broth or to a fraction of the fermentation broth.

The fraction of the fermentation broth may be obtained by filtration, preferably by microfiltration, or by centrifugation, preferably by decanter centrifugation, disc stack centrifugation or a nozzle separator. A fraction of the fermentation broth may also be obtained by removing a part of the fermentation broth present in the fermenter.

In a preferred embodiment, the fraction of the fermentation broth is selected from (i) the spin-down fraction obtained by centrifugation of the fermentation broth, and (ii) the supernatant obtained by centrifugation of the fermentation broth. Preferably, the supernatant is used in the method of the present invention.

In another preferred embodiment, the fraction of the fermentation broth may be the filtrate/retentate obtained by filtration of the fermentation broth. The filtration may be dead-end or crossflow filtration.

Further, one or more flocculation agents may be added to the fermentation broth. The flocculation agent(s) may be added to the fermentation broth before separation of the cells. Flocculation agents are known in the art and are especially used to provide a protein solution (e.g. a fermentation broth) which is particularly well fitted for centrifugation, filtration or for membrane concentration/filtration. A suitable flocculation agent may be any soluble Fe or Al compound. Use of such soluble Fe and/or Al compounds as flocculation agent(s) are known from WO 96/38469. Any soluble Fe or Al compound, or any mixture thereof, may be used, such as $Al_2(SO_4)_3$, $NaAlO_2$, $K_2Al_2O_4$, $AlCl_3$, Al-acetate, Al-formate, $Fe_2(SO_4)_3$, Fe(III)-formate, Fe(III)-acetate, Fe(II)-formate and Fe(II)-acetate. Preferably the compound is a polymer aluminum chlorohydrate (e.g., PAX-18 available from Kemira) or $Al_2(SO_4)_3$. Further suitable flocculation agents include organic polymers, such as Superfloc C-521 and Superfloc A-130 (available form Kemira), which are cationic and anionic organic polymers, respectively, of different molecular weights.

In another embodiment, the method of the present invention does not comprise adding a trivalent or polymeric flocculation agent to the fermentation broth. In another embodiment, the solution containing the salt of the divalent cation which is added in step a) of the method of the present invention does not contain a flocculating agent. Preferably, the solution containing the salt of the divalent cation which is added in step a) of the method of the present invention does not contain a polymeric flocculating agent, like Superfloc C-521 and Superfloc A-130.

Method Step a) Adding a Salt of a Divalent Cation

In an embodiment of the invention, the divalent cation is selected from $Ca^{2+}$, $Mg^{2+}$, $Ba^{2+}$, $Pb^{2+}$, $Fe^{2+}$, $Zn^{2+}$, $Ni^{2+}$, $Cu^{2+}$, $Mn^{2+}$, $Sr^{2+}$, $Co^{2+}$, $Be^{2+}$ and $Ra^{2+}$. Preferred divalent cations according to the present invention include Group IIA elements (alkaline earth metals), i.e. $Ca^{2+}$, $Mg^{2+}$, $Sr^{2+}$, $Ba^{2+}$, $Ra^{2+}$, $Be^{2+}$. Particularly preferred divalent cations are $Ca^{2+}$ and $Mg^{2+}$ and the most preferred divalent cation is $Ca^{2+}$.

In a further embodiment of the invention, the salt of the divalent cation is the chloride, phosphate, sulfate, nitrate, formate or acetate salt of the divalent cation such as calcium chloride, calcium phosphate, calcium sulfate, calcium nitrate, calcium acetate, magnesium chloride, magnesium phosphate, magnesium sulfate, magnesium nitrate or magnesium acetate. Preferably, the salt of the divalent cation is calcium chloride ($CaCl_2$) or magnesium chloride ($MgCl_2$), more preferably, the salt of the divalent cation is $CaCl_2$. In another embodiment, the salt of the divalent cation is calcium formate or calcium acetate or magnesium formate or acetate.

In an embodiment, the divalent salt is added to the fermentation broth or a fraction thereof in a concentration of 0.01-5%, 0.01-4%, 0.01-3%, 0.01-2% or 0.01-1% of the fermentation broth (w/w), in particular 0.01-1% of the fermentation broth (w/w). Preferably the divalent salt is added to the fermentation broth or a fraction thereof in a concentration of 0.1-1%, more preferably in a concentration of 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95% or 1% of the fermentation broth (w/w). Most preferably the divalent salt is added to the fermentation broth or a fraction thereof in a concentration of 0.75% of the fermentation broth (w/w). The divalent salt is typically added either in-line, or in a stirred tank, or by any other method known in the art.

In an embodiment, the divalent salt is added to the fermentation broth or a fraction thereof in at least stoichiometric amounts of the divalent cation to phosphate ions. Preferably, the molar ratio between the divalent cation and the phosphate ions is greater than 1, such as between 2 and 10, more preferably between 2 and 5. Hence, the molar ratio between the divalent cation and the phosphate ions is 2, 3, 4, 5, 6, 7, 8, 9, or 10, preferably 2, 3, 4, or 5, most preferably 2 or 3. The divalent salt is typically added either in-line, or in a stirred tank, or by any other method known in the art.

The final amount of added divalent cation may depend on the amount of phosphate in the fermentation broth present at the end of the fermentation process. As discussed above, it is believed that after increasing the pH the phosphate remaining in the fermentation broth will extract divalent cations from the enzymes present in the fermentation broth. This means, the more phosphate present in the fermentation broth prior to protein recovery the higher is the amount of divalent cation salt which has to be added to the broth. Phosphate may be added at the beginning of the fermentation process to the fermentation medium and will be consumed by the cultured microorganism. Depending on the fermentation protocol, additional phosphate may be fed during the culture. Therefore, the phosphate remaining at the end of the fermentation process depends on the fermentation protocol.

In a preferred embodiment, the fermentation broth comprises phosphate, when the salt of the divalent cation is added. The amount of phosphate present in the fermentation broth can be determined by any means known in the art, e.g. by analytical HPLC. The concentration of phosphate at the end of the fermentation process may be 0-5 g/L, 0-4 g/L, 0-3 g/L, 0-2 g/L or 0-1 g/L. The concentration of phosphate at the end of the fermentation process may be 0.1-3 g/L or 0.2-3 g/l or 0.1-1 g/L or 0.2-1 g/L. Preferably, in the method of the present invention the phosphate concentration in the solution comprising the protein of interest, e.g., the fermentation broth or a fraction thereof, does not exceed 10 mmol after the addition of the salt of the divalent cation. Preferably, in the method of the present invention the phosphate concentration in the fermentation broth or a fraction thereof does not exceed 10 mmol after the addition of the salt of the divalent cation. Preferably, no phosphate is added to the fermentation broth or a fraction thereof after completion of the fermentation process except by the addition of a phosphate containing salt of the divalent cation. Preferably, no phosphate is added to the fermentation broth or a fraction thereof after completion of the fermentation process. Most preferably, the fermentation broth or a fraction thereof prior to the addition of the divalent cation comprises phosphate in a concentration that does not exceed 10 mmol and no phosphate is added to the fermentation broth or a fraction thereof after completion of the fermentation process.

Method Step b) Adjusting the pH

According to the invention, simultaneously to step a) or after the salt of a divalent cation has been added to the fermentation broth or a fraction thereof, the pH of the fermentation broth is adjusted to a pH value above 11. Preferably the pH is adjusted to a value of at least pH 11.1, at least pH 11.2, at least pH 11.3, at least pH 11.4, or at least pH 11.5, preferably of at least pH 11.5. Preferably the pH is adjusted to a value of between pH 11 and pH 13, e.g. to a pH of 11.2, 11.5, 12.0, 12.5, or 12.7, more preferable to a value between pH 11.0 and pH 12.5, e.g., to a pH of 11.1, 11.2, 11.3, 11.4, 11.5, 11.6, 11.7, 11.8, 11.9, 12.0, 12.1, 12.2, 12.3, or 12.4. Preferably the pH is adjusted to a value of more than pH 11 to at most pH 13.0, e.g. to a pH of 11.2, 11.5, 12.0, 12.2, 12.5, pH 12.7, or pH 13.0, preferably the pH is adjusted to a value of more than pH 11 to at most pH 12.5, e.g. to a pH of 11.2, 11.5, 12.0, 12.2, or 12.5, preferably the pH is adjusted to a value of more than pH 11 to at most pH 12.0, e.g. to a pH of 11.2, 11.5, 11.7, or 12.0. Preferably, the pH is adjusted to pH 11.1 to pH 13, pH 11.1 to pH 12.5, pH 11.1 to pH 12, pH 11.2 to pH 13, pH 11.2 to pH 12.5, pH 11.2 to pH 12, pH 11.5 to pH 13, pH 11.5 to pH 12.5, or pH 11.5 to pH 12. Preferably, the pH of the fermentation broth is adjusted to a pH value above 11.0, such as a pH of 11.2, 11.5, 12, 12.5 or 13, preferably to a pH of more than 11.0 to at most 12.0, such as a pH of 11.1, 11.2, 11.3, 11.4, 11.5, 11.6, 11.7, 11.8, 11.9 or 12.0, after the salt of a divalent cation has been added to the fermentation broth, i.e. step a) is performed before step b).

The pH may be adjusted by using any suitable strategy known to the person skilled in the art. Any suitable base or basic solution may be used to adjust the pH. Preferred bases are sodium hydroxide, potassium hydroxide and ammonium hydroxide. In a preferred embodiment of the invention, the pH is adjusted by adding NaOH.

In another embodiment of the invention, the method steps of:

a) adding a salt of a divalent cation to the fermentation broth or a fraction thereof comprising the protein of interest, and
b) adjusting the pH of the fermentation broth to more than pH 11 may be performed simultaneously or step a) is performed prior to step b).

Preferably, step a) is performed prior to step b). Step b) does not have to immediately follow step a). Hence, in one embodiment, step b) is performed 10 minutes, 20 minutes, 30 minutes, 40 minutes, 50 minutes, one hour, two hours or three hours after completion of step a).

If steps a) and b) are performed simultaneously, a continuous and rapid mixing of the fermentation broth, the divalent cation salt and the added base is required so that the protein does not come into contact with high concentrations of the base in the absence of the divalent cation. It is thus recommended to minimize local pH peaks to prevent reduction in protein activity and/or stability by thorough mixing of the fermentation broth, the divalent cation salt and the added base. This may also be achieved by in-line mixing.

In another embodiment, an additional step may be performed between step a) and step b). The additional step may be the addition of compounds such as flocculation agents, filtration aids/additives, activated charcoal, decolorants and the like.

After adding the divalent salt and adjusting the pH, the fermentation broth is constantly stirred over a predetermined incubation time. The incubation time may vary from 1 to 120 minutes. The incubation time may be 1 minute, 10 minutes, 20 minutes, 30 minutes, 40 minutes, 50 minutes, 60 minutes, 70 minutes, 80 minutes, 90 minutes, 100 minutes, 110 minutes, 110 minutes, or 120 minutes. Preferably, the incubation time is between 60-90 minutes, most preferably, the incubation time is 60 minutes. If the pH is adjusted by in-line addition of the base, the incubation time is up to 10 minutes, preferably up to 5 minutes, most preferably up to 1 minute.

During this incubation time, solubilization of protein crystals and/or protein precipitates and/or protein bound to cells/insoluble is promoted. Hence, at the end of the incubation time the protein is present in soluble form.

As mentioned above, the incubation at a high pH leads to the dissolution of crystallized or precipitated protein (see also Example 1). However, high pH treatment may have a negative effect on the stability and thus may have detrimental effects on the activity of the protein to be purified, e.g. an enzyme. The addition of a divalent cation to the fermentation broth stabilizes the protein of interest and preserves its activity and stability (see Examples 2 and 3).

By using the method of the present invention, the enzyme substantially retains its activity when the pH of the fermentation broth or fraction thereof is increased. The term "substantially retains its activity" means that the activity of the enzyme after the pH increase is at least 70%, at least 75%, at least 80%, at least 81%, at least 82%, at least 83%, at least 84% or at least 85% of the activity of the enzyme before the pH increase, preferably the activity of the enzyme after the pH increase is at least 86%, at least 87%, at least 88%, at least 89%, at least 90%, at least 91%, at least 92%, at least 93% or at least 94% of the activity of the enzyme before the pH increase and more preferably the activity of the enzyme after the pH increase is at least at least 95%, at least 96%, at least 97% or at least 98% of the activity of the enzyme before the pH increase. Methods to determine enzyme activity are discussed below in the context of the enzymes which may be used in the present invention.

"Stabilization of the enzyme" means that the enzyme substantially retains its conformation and therefore also its activity as described above.

In one embodiment, the fermentation broth, or the fraction thereof, may be diluted before or after the method of the invention is performed. The fermentation broth comprising the protein of interest may be diluted 100-2000% (w/w), preferably 100-1500% (w/w), more preferably 100-1000% (w/w), in particular 200-700% (w/w). The fermentation broth may be diluted with water.

In an alternative embodiment, the fermentation broth is not diluted before the method of the invention is performed.

Fermentation Process

In an embodiment, the inventive methods further comprise prior to step a) and b) the fermentation of a host cell, preferably the fermentation of a microorganism.

The fermentation process may be of any known set-up, such as a batch process, a fed-batch process or a continuous fermentation process.

A batch fermentation is a process where the growth medium is provided in the fermenter from the start, where the fermenter is inoculated with an intended microbial cell and the fermentation process is running until a predetermined condition has been reached, typically depletion of the growth medium and the cessation of microbial growth caused by the depletion.

A fed-batch fermentation is a process where a part of the growth medium is provided from the start of the fermentation process where the inoculum is added, and at a certain time point after the start of the fermentation additional substrate, the feed medium, is fed to the fermenter at a rate that may be predetermined or determined by the conditions in the fermenter, until the maximal volume has been reached. The feed medium may or may not have the same composition as the initial growth medium.

A continuous fermentation is a process where new growth medium is continuously fed to the fermenter and fermentation broth is simultaneously removed from the fermenter at the same rate so the volume in the fermenter is constant. In industrial fermentation processes are typically conducted by first providing a growth medium in a fermenter, inoculating the fermenter with an inoculum comprising a microbial cell and fermenting under defined conditions such as pH, temperature, oxygen level etc., at a predefined time or until a predefined condition, e.g. titer, oxygen consumption, has been reached.

In a preferred embodiment, a fed-batch fermentation process is performed prior to steps a) and b) of the method of the present invention.

The inoculum is in general a liquid culture of the microorganism used for the fermentation prepared in a seed fermenter, a seed fermenter typically having a volume of 5-15% of the main fermenter used for production. The growth medium for the seed fermenter may or may not be the same growth medium as used in the main fermenter.

Thus the inoculum is typically prepared from a vial containing the production strain of the host cell (preferably a microorganism), where the content of the vial first is inoculated in a small volume and the host cells are grown to a desired density to prepare a first culture of the production strain, where after the first culture the production strain is inoculated in the next of a series of seed fermenters of increasing size, where the volume increases 5-20 fold in each step until a sufficient volume to inoculate the production fermenter has been reached. Such a series of fermenters in increasing size is also known as a seed train (WO2017/068012 A1).

Thus, during the fermentation process, a microorganism comprising a nucleic acid sequence encoding the protein of interest is inoculated and cultivated in a fermentation medium. Preferably, the microorganism is a recombinant microorganism.

Any medium suitable for the culture of the particular microbial cell may be used. The fermentation medium may be a minimal medium as described before, e.g., in WO 98/37179, or the fermentation medium may be a complex medium comprising complex nitrogen and/or carbon sources, wherein the complex nitrogen source may be partially hydrolyzed as described in WO 2004/003216. Furthermore, the fermentation medium may contain a phosphate and/or carbonate source. The phosphate can be added to the fermentation medium in chemically defined form by adding one or more phosphate salts such as potassium phosphate, sodium phosphate, magnesium phosphate and combinations thereof.

The concentration of phosphate in the fermentation medium at the beginning of the culture process may be between 2 and 19 g/L of the initial fermentation medium.

The present invention may be useful for recovering a protein from any fermentation process in industrial scale, i.e., at least 1,000 liters, more preferably at least 5,000 liters, even more preferably at least 50,000 liters.

Downstream Processing

After the method of the present invention has been performed, the resulting protein may be further purified by methods known in the art. For example, the protein may be recovered by conventional procedures including, but not limited to, filtration, e.g., ultra-filtration and micro-filtration, centrifugation, e.g. with a nozzle separator, extraction, spray-drying, evaporation, precipitation or crystallization.

The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). The purified polypeptide may then be concentrated by procedures known in the art including, but not limited to, ultrafiltration and evaporation, in particular, thin film evaporation.

Protein Formulation

In another embodiment of the invention, the inventive methods further comprise a step d) of preparing a formulation containing the protein of interest.

"Protein formulation" means any non-complex formulation comprising a small number of ingredients, wherein the ingredients serve the purpose of stabilizing the proteins comprised in the protein formulation and/or the stabilization of the protein formulation itself. The term "protein stability" relates to the retention of proteins activity as a function of time during storage or operation. The term "protein formulation stability" relates to the maintenance of physical appearance of the protein formulation during storage or operation as well as the avoidance of microbial contamination during storage or operation.

The protein formulation can be either solid or liquid. Protein formulations can be obtained by using techniques known in the art. For instance, without being limited thereto, solid enzyme formulations can be obtained by extrusion or granulation. Suitable extrusion and granulation techniques are known in the art and are described for instance in WO 94/19444 A1 and WO 97/43482 A1.

Host Cell

According to the invention, the protein of interest may be obtained from any host cell. The host cell may be a eukaryotic or a prokaryotic cell.

In a preferred embodiment, the host cell may be a microorganism or microbial cell. In one embodiment, the microorganism is a bacteria, an archaea, a fungal cell or a yeast cell.

In an embodiment of the invention, the host cell may be a bacterium.

Bacterial cells include gram positive or gram negative bacteria. Preferably, the bacterial cells are gram-positive. Gram-positive bacteria include, but are not limited to, *Bacillus, Brevibacterium, Corynebacterium, Streptococcus, Streptomyces, Staphylococcus, Enterococcus, Lactobacillus, Lactococcus, Clostridium, Geobacillus*, and *Oceanobacillus*.

In the methods of the present invention, the bacterial cell may be any *Bacillus* cell. *Bacillus* cells useful in the practice of the present invention include, but are not limited to, *Bacillus alkalophilus, Bacillus amyloliquefaciens, Bacillus brevis, Bacillus circulars, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus,*

*Bacillus cereus Bacillus paralicheniformis, Bacillus subtilis,* and *Bacillus thuringiensis* cells. In one embodiment, the bacterial host cell is a *Bacillus amyloliquefaciens, Bacillus lentus, Bacillus licheniformis, Bacillus stearothermophilus* or *Bacillus subtilis* cell. In another embodiment, the bacterial host cell is a *Bacillus licheniformis* cell or a *Bacillus subtilis* cell. In one embodiment, the *Bacillus* cell is a *Bacillus* cell of *Bacillus* sub ti/is, *Bacillus pumilus, Bacillus licheniformis*, or *Bacillus lentus*. Preferably, the cell is a *Bacillus licheniformis* cell.

In the methods of the present invention, the bacterial cell may be *Lactobacillus acidophilus, Lactobacillus plantarum, Lactobacillus gasseri, Lactobacillus bulgaricusk, Lactobacillus reuteri, Escherichia coli, Staphylococcus aureus, Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola, Corynebacterium effiziens, Corynebacterium efficiens, Corynebacterium deserti, Brevibacterium flavum, Brevibacterium lactofermentum, Brevibacterium divarecatum, Pseudomonas putida, Pseudomonas syringae, Streptomyces coelicolor, Streptomyces lividans, Streptomyces albus, Streptomyces avermitilis, Gluconobacter oxydans, Gluconobacter morbifer, Gluconobacter thailandicus, Acetobacter aceti, Clostridium acetobutylicum, Clostridium saccharobutylicum, Clostridium beijerinckii, Streptococcus equisimilis, Streptococcus pyogenes, Streptococcus uberis, Streptococcus equi* subsp., *Zooepidemicus* or *Basfia succiniciproducens*.

Some other preferred bacteria include strains of the order Actinomycetales, preferably, *Streptomyces*, preferably *Streptomyces spheroides* (ATTC 23965), *Streptomyces thermoviolaceus* (IFO 12382), *Streptomyces lividans* or *Streptomyces murinus* or *Streptoverticillum verticillium* ssp. *verticillium*. Other preferred bacteria include *Rhodobacter sphaeroides, Rhodomonas palustri, Streptococcus lactis*. Further preferred bacteria include strains belonging to *Myxococcus*, e.g., *M. virescens*.

Gram-negative bacteria include, but are not limited to, *Escherichia, Pseudomonas, Salmonella, Campylobacter, Helicobacter, Acetobacter, Flavobacterium, Fusobacterium, Gluconobacter*. In a specific embodiment, the bacterial host cell is a *Escherichia coli* cell. Another gram negative bacteria is *Pseudomonas purrocinia* (ATCC 15958) or *Pseudomonas fluorescens* (NRRL B-11), or *Basfia succiniciproducens*. Further the gram-negative Bacteria include *Butiauxella*, more specifically *Butiauxella agrestis, Butiauxella brennerae, Butiauxella ferragutiae, Butiauxella gaviniae, Butiauxella izardii, Butiauxella noackiae*, and *Butiauxella warmboldiae*.

In a specific embodiment, the microorganism may be of the genus *Bacillus, Streptomyces, Escherichia, Buttiauxella* and *Pseudomonas*.

The microbial cell may be a fungal cell. "Fungi" as used herein includes the phyla *Ascomycota, Basidiomycota, Chytridiomycota*, and *Zygomycota* as well as the *Oomycota* and *Deuteromycotina* and all mitosporic fungi. Representative groups of *Ascomycota* include, e.g., *Neurospora, Eupenicillium* (=*Penicillium*), *Emericella* (=*Aspergillus*), *Eurotium* (=*Aspergillus*), *Myceliophthora*, C1, and the true yeasts listed below. Examples of Basidiomycota include mushrooms, rusts, and smuts. Representative groups of *Chytridiomycota* include, e.g., *Allomyces, Blastocladiella, Coelomomyces*, and aquatic fungi. Representative groups of *Oomycota* include, e.g. *Saprolegniomycetous aquatic fungi* (water molds) such as *Achlya*. Examples of mitosporic fungi include *Aspergillus*, e.g., *Aspergillus niger, Penicillium, Candida*, and *Alternaria*. Representative groups of *Zygomycota* include, e.g., *Rhizopus* and *Mucor*.

Some preferred fungi include strains belonging to the subdivision *Deuteromycotina*, class *Hyphomycetes*, e.g., *Fusarium, Humicola, Tricoderma, Myrothecium, Vertialum, Arthromyces, Caldariomyces, Ulocladium, Embellisia, Cladosporium* or *Dreschlera*, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision *Basidiomycotina*, class *Basidiomycetes*, e.g. *Coprinus, Phanerochaete, Coriolus* or *Trametes*, in particular *Coprinus cinereus* f *microsporus* (IFO 8371), *Coprinus macrorhizus, Phanerochaete chrysosporium* (e.g. NA-12) or *Trametes* (previously called *Polyporus*), e.g. *T. versicolor* (e.g. PR4 28-A).

Further preferred fungi include strains belonging to the subdivision *Zygomycotina*, class *Mycoraceae*, e.g. *Rhizopus* or *Mucor*, in particular *Mucor hiemalis*.

The microbial cell may be a yeast cell. "Yeast" as used herein includes ascosporogenous yeast (*Endomycetales*), basidiosporogenous yeast, and yeast belonging to the *fungi imperfecti* (*Blastomycetes*). The ascosporogenous yeasts are divided into the families *Spermophthoraceae* and *Saccharomycetaceae*. The latter is comprised of four subfamilies, *Schizosaccharomycoideae* (e.g., genus *Schizosaccharomyces*), *Nadsonioideae, Lipomycoideae*,and *Saccharomycoideae* (e.g. genera *Kluyveromyces, Pichia*, and *Saccharomyces*). The basidiosporogenous yeasts include the genera *Leucosporidim, Rhodosporidium, Sporidiobolus, Filobasidium*, and *Filobasidiella*. Yeasts belonging to the Fungi Imperfecti are divided into two families, *Sporobolomycetaceae* (e.g., genera *Sporobolomyces* and *Bullera*) and *Cryptococcaceae* (e.g. genus *Candida*). In another embodiment, the fungal host cell is a filamentous fungal cell, e.g., *Ashbya* spec, preferably *Ashbya gossypii*(*Eremothecium gossypii*).

Preferably, the fungal strain is selected from the group consisting of *Aspergillus niger, Trichoderma reesei* and *Pichia pastoris*.

In an embodiment, the host cell may also be a eukaryote, such as a mammalian cell, an insect cell, or a plant cell.

In one embodiment, the cell comprises one or more genetic constructs for heterologous gene expression.

Protein of Interest

The present invention involves a process for recovering a microorganism in order to produce a protein of interest.

In a preferred embodiment, the protein of interest is an enzyme.

The enzyme may have one or more binding sites for a divalent cation. The enzyme thus may have a binding site for $Ca^{2+}$, $Mg^{2+}$, $Ba^{2+}$, $Pb^{2+}$, $Fe^{2+}$, $Zn^{2+}$, $Ni^{2+}$, $Mn^{2+}$, $Sr^{2+}$, $Co^{2+}$, $Be^{2+}$ or $Ra^{2+}$. Preferably, the enzyme has a binding site for $Ca^{2+}$ and/or $Mg^{2+}$. Enzymes having a binding site for $Ca^{2+}$ and/or $Mg^{2+}$ are known to the skilled person. Preferably, the enzyme is a protease or an amylase. The protease is preferably an alkaline protease, preferably a serine-protease, more preferably a subtilisin protease. The amylase is preferably an alpha-amylase.

Further, the enzyme may have an isoelectric point (pI) below pH 11. Preferably, the pI pf the enzyme is one pH unit, more preferably two pH units below pH 11. The isoelectric point of an enzyme is the pH at which the enzyme carries no net electrical charge or is electrically neutral in the statistical mean. The pI may be determined by methods known in the art, e.g. by gel electrophoresis using a buffer which determines the pH of the electrophoretic gel. If the pH of the buffer is above the pI of the protein being analyzed, the protein will migrate to the positive pole. If the pH of the buffer is below the pI of the protein being analyzed, the protein will migrate to the negative pole of the gel. If the buffer pH is equal to the pI of the protein being analyzed, the protein will not migrate within the gel at all.

In another embodiment, the enzyme is stable at a pH above pH 11. An enzyme is stable at a certain pH, if the enzyme retains its native folded conformation, i.e. is not in a denatured (unfolded or extended) state.

In a preferred embodiment, the enzyme is selected from the group consisting of amylase, alpha-amylase, glucoamylase, pullulanase, protease, metalloprotease, peptidase, lipase, cutinase, acyl transferase, cellulase, endoglucanase, glucosidase, cellubiohydrolase, xylanase, xyloglucantransferase, xylosidase, mannanase, phytase, phosphatase, xylose isomerase, glucoase isomerase, lactase, acetolactate decarboxylase, pectinase, pectin methylesterase, polygalacturonidase, lyase, pectate lyase, arabinase, arabinofuranosidase, galactanase, a laccase, peroxidase and an asparaginase, preferably wherein the enzyme is an amylase or protease.

In a particular preferred embodiment, the following enzymes are preferred:

Protease

Enzymes having proteolytic activity are called "proteases" or "peptidases". Proteases are active proteins exerting "protease activity" or "proteolytic activity".

Proteases are members of class EC 3.4. Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include, but are not limited, to Lavergy™ Pro (BASF); Alcalase®, Blaze®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect® Prime, Purafect MA®, Purafect Ox®, Purafect OxP®, Puramax®, Properase®, FN2®, FN3®, FN4®, Excellase®, Eraser®, Utimase®, Opticlean®, Effectenz®, Preferenz® and Optimase® (Danisco/DuPont), Axapem™ (Gist-Brocases N.V.), Bacillus lentusAlkaline Protease, and KAP (Bacillus alkalophilus subtilisin) from Kao.

In one embodiment the protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36, EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119) plasmin (e.g., EC 3.4.21.7), trypsin (e.g., EC 3.4.21.4), thrombin (e.g., EC 3.4.21.5) and subtilisin (also known as subtilopeptidase, e.g., EC 3.4.21.62), the latter hereinafter also being referred to as "subtilisin".

A sub-group of the serine proteases tentatively designated subtilases has been proposed by Siezen et al. (1991), Protein Eng. 4:719-737 and Siezen et al. (1997), Protein Science 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997), Protein Science 6:501-523.

The subtilases may be divided into 6 sub-divisions, i.e. the subtilisin family, thermitase family, the proteinase K family, the lantibiotic peptidase family, the kexin family and the pyrolysin family.

A subgroup of the subtilases are the subtilisins, which are serine proteases from the family S8 as defined by the MEROPS database (accessible under merops.sanger.ac.uk). Peptidase family S8 contains the serine endopeptidase subtilisin and its homologues. In subfamily S8A, the active site residues frequently occur in the motifs Asp-Thr/Ser-Gly, His-Gly-Thr-His and Gly-Thr-Ser-Met-Ala-Xaa-Pro. Most members of the peptidase family S8 are active at neutral-mildly alkali pH. Many peptidases in the family are thermostable.

Prominent members of family S8, subfamily A are:

| name | MEROPS Family S8, Subfamily A |
|---|---|
| Subtilisin Carlsberg | S08.001 |
| Subtilisin lentus | S08.003 |
| Thermitase | S08.007 |
| Subtilisin BPN' | S08.034 |
| Subtilisin DY | S08.037 |
| Alkaline peptidase | S08.038 |
| Subtilisin ALP 1 | S08.045 |
| Subtilisin sendai | S08.098 |
| Alkaline elastase YaB | S08.157 |

Proteases of the subtilisin type (EC 3.4.21.62) and variants may be bacterial proteases. Said bacterial protease may be from a Gram-positive bacterium such as Bacillus, Clostridium, Enterococcus, Geobacillus, Lactobacillus, Lactococcus, Oceanobacillus, Staphylococcus, Streptococcus, or Streptomyces, or a Gram-negative bacterium such as a Campylobacter, E. coli, Flavobacterium, Fusobacterium, Helicobacter, Ilyobacter, Neisseria, Pseudomonas, Salmonella, or Ureaplasma. A review of this family is provided, for example, in "Subtilases: Subtilisin-like Proteases" by R. Siezen, pages 75-95 in "Subtilisin enzymes", edited by R. Bott and C. Betzel, New York, 1996.

At least one protease may be selected from the following: subtilisin from Bacillus amyloliquefaciens BPN' (described by Vasantha et al. (1984) J. Bacteriol. Volume 159, p. 811-819 and JA Wells et al. (1983) in Nucleic Acids Research, Volume 11, p. 7911-7925); subtilisin from Bacillus licheniformis (subtilisin Carlsberg; disclosed in EL Smith et al. (1968) in J. Biol Chem, Volume 243, pp. 2184-2191, and Jacobs et al. (1985) in Nucl. Acids Res, Vol 13, p. 8913-8926); subtilisin PB92 (original sequence of the alkaline protease PB92 is described in EP 283075 A2); subtilisin 147 and/or 309 (Esperase®, Savinase®, respectively) as disclosed in WO 89/06279; subtilisin from *Bacillus lentus* as disclosed in WO 91/02792, such as from *Bacillus lentus* DSM 5483 or the variants of *Bacillus lentus* DSM 5483 as described in WO 95/23221; subtilisin from *Bacillus alcalophilus* (DSM 11233) disclosed in DE 10064983; subtilisin from *Bacillus gibsonii*(DSM 14391) as disclosed in WO 2003/054184; subtilisin from *Bacillus* sp. (DSM 14390) disclosed in WO 2003/056017; subtilisin from *Bacillus* sp. (DSM 14392) disclosed in WO 2003/055974; subtilisin from *Bacillus gibsonii* (DSM 14393) disclosed in WO 2003/054184; subtilisin having SEQ ID NO: 4 as described in WO 2005/063974; subtilisin having SEQ ID NO: 4 as described in WO 2005/103244; subtilisin having SEQ ID NO: 7 as described in WO 2005/103244; and subtilisin having SEQ ID NO: 2 as described in application DE 102005028295.4.

Proteases also include the variants described in: WO 92/19729, WO 95/23221, WO 96/34946, WO 98/20115, WO 98/20116, WO 99/11768, WO 01/44452, WO 02/088340, WO 03/006602, WO 2004/03186, WO 2004/041979, WO 2007/006305, WO 2011/036263, WO 2011/036264, and WO 2011/072099. Suitable examples comprise especially protease variants of subtilisin protease derived from SEQ ID NO:22 as described in EP 1 921 147 with amino acid substitutions in one or more of the following positions: 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and 274 which have proteolytic activity. In addition, a subtilisin protease is not mutated at positions Asp32, His64 and Ser221.

A subtilisin-like enzyme may have SEQ ID NO:22 as described in EP 1921147, or may be a variant thereof which is at least 80%, at least 90%, at least 95% or at least 98% identical to SEQ ID NO:22 as described in EP 1 921 147 and has proteolytic activity. In one embodiment, a subtilisin-like enzyme is at least 80%, at least 90%, at least 95% or at least 98% identical to SEQ ID NO:22 as described in EP 1 921 147 and is characterized by having amino acid glutamic acid (E), or aspartic acid (D), or asparagine (N), or glutamine (Q), or alanine (A), or glycine (G), or serine (5) at position 101 (according to BPN' numbering) and has proteolytic activity. In one embodiment, a subtilisin-like enzyme is at least 80%, at least 90%, at least 95% or at least 98% identical to SEQ ID NO:22 as described in EP 1 921 147 and is characterized by having amino acid glutamic acid (E), or aspartic acid (D), at position 101 (according to BPN' numbering) and has proteolytic activity. Such a subtilisin variant may comprise an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, said protease comprises one or more further substitutions (a) to (h): (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h).

A subtilisin-like enzyme may have an amino acid sequence being at least 80% identical to SEQ ID NO:22 as described in EP 1 921 147 and being further characterized by comprising the substitution R101E, and one or more substitutions selected from the group consisting of S156D, L262E, Q137H, S3T, R45E,D,Q, P55N, T58W,Y,L, Q59D, M,N,T, G61 D,R, S87E, G97S, A98D,E,R, S106A,W, N117E, H120V,D,K,N, S125M, P129D, E136Q, S144W, S161T, S163A,G, Y171 L, A172S, N185Q, V199M, Y209W, M222Q, N238H, V244T, N261T,D and L262N, Q,D (as described in WO 2016/096711 and according to the BPN' numbering), and has proteolytic activity.

Proteases used in the present invention have proteolytic activity. The methods for determining proteolytic activity are well-known in the literature (see e.g. Gupta et al. (2002), Appl. Microbiol. Biotechnol. 60: 381-395). Proteolytic activity may be determined by using Succinyl-Ala-Ala-Pro-Phe-p-nitroanilide (Suc-AAPF-pNA, short AAPF; see e.g. DelMar et al.

(1979), Analytical Biochem 99, 316-320) as substrate. pNA is cleaved from the substrate molecule by proteolytic cleavage, resulting in release of yellow color of free pNA which can be quantified by measuring OD405.

Amylase

Alpha-amylase (E.G. 3.2.1.1) enzymes may perform endohydrolysis of (1->4)-alpha-D-glucosidic linkages in polysaccharides containing three or more (1->4)-alpha-linked D-glucose units. Amylase enzymes act on starch, glycogen and related polysaccharides and oligosaccharides in a random manner; reducing groups are liberated in the alpha-configuration. Other examples of amylase enzymes include: Beta-amylase (E.C. 3.2.1.2), Glucan 1,4-alpha-maltotetraohydrolase (E.c. 3.2.1.60), Isoamylase (E.C. 3.2.1.68), Glucan 1,4-alpha-maltohexaosidase (E.C. 3.2.1.98), and Glucan 1,4-alpha-maltohydrolase (E.C. 3.2.1.133).

Amylase enzymes have been described in patent documents including, but not limited to: WO 2002/068589, WO 2002/068597, WO 2003/083054, WO 2004/091544, and WO 2008/080093.

An amylase derived from *Bacillus licheniformis* has SEQ ID NO:2 as described in WO 95/10603. Suitable variants of this amylase are those which are at least 90% identical to SEQ ID NO: 2 as described in WO 95/10603 and/or comprise one or more substitutions in the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 and have amylolytic activity. Such variants are described in WO 94/02597, WO 94/018314, WO 97/043424 and SEQ ID NO:4 of WO 99/019467.

An amylase derived from *B. stearothermophilus* has SEQ ID NO:6 as described in WO 02/10355. Suitable variants of this amylase are those which are at least 90% identical thereto and have amylolytic activity. Suitable variants of SEQ ID NO:6 include those which are at least 90% identical to SEQ ID NO:6 as described in WO 02/10355 and/or further comprise a deletion in positions 181 and/or 182 and/or a substitution in position 193.

An amylase derived from *Bacillus* sp. 707 has SEQ ID NO:6 as disclosed in WO 99/19467 or is at least 90% identical thereto having amylolytic activity.

An amylase derived from *Bacillus halmapalus* has SEQ ID NO:2 or SEQ ID NO:7 as described in WO 96/23872, also described as SP-722, or is at least 90% identical to one of the sequences which has amylolytic activity.

An amylase derived from *Bacillus* sp. DSM 12649 has SEQ ID NO:4 as disclosed in WO 00/22103 or is at least 90% identical thereto having amylolytic activity.

An amylase derived from *Bacillus* strain TS-23 has SEQ ID NO:2 as disclosed in WO 2009/061380 or is at least 90% identical thereto having amylolytic activity.

An amylase derived from *Cytophaga* sp. has SEQ ID NO:1 as disclosed in WO 2013/184577 or is at least 90% identical thereto having amylolytic activity.

An amylase derived from *Bacillus megaterium* DSM 90 has SEQ ID NO:1 as disclosed in WO 2010/104675 or is at least 90% identical thereto having amylolytic activity.

Amylases are known having amino acids 1 to 485 of SEQ ID NO:2 as described in WO 00/60060 or amylases comprising an amino acid sequence which is at least 96% identical to amino acids 1 to 485 of SEQ ID NO:2 which have amylolytic activity. Amylases are also known having SEQ ID NO: 12 as described in WO 2006/002643 or amylases having at least 80% identity thereto and have amylolytic activity. Suitable amylases include those having at least 80% identity compared to SEQ ID NO:12 and/or comprising the substitutions at positions Y295F and M202LITV and have amylolytic activity.

Amylases are also known having SEQ ID NO:6 as described in WO 2011/098531 or amylases having at least 80% identity thereto having amylolytic activity. Suitable amylases include those having at least 80% identity compared to SEQ ID NO:6 and/or comprising a substitution at one or more positions selected from the group consisting of 193 [G,A,S,T or M], 195 [F,W,Y,L,I or V], 197 [F,W,Y,L,I or V], 198 [Q or N], 200 [F,W,Y,L,I or V], 203 [F,W,Y,L,I or V], 206 [F,W,Y,N,L,I,V,H,Q,D or E], 210 [F,W,Y,L,I or V], 212 [F,W,Y,L,I or V], 213 [G,A,S,T or M] and 243 [F,W,Y, L,I or V] and have amylolytic activity.

Amylases are known having SEQ ID NO:1 as described in WO 2013/001078 or amylases having at least 85% identity thereto having amylolytic activity. Suitable amylases include those having at least 85% identity compared to SEQ ID NO:1 and/or comprising an alteration at two or more (several) positions corresponding to positions G304, W140, W189, D134, E260, F262, W284, W347, W439, W469, G476, and G477 and having amylolytic activity.

Amylases are known having SEQ ID NO:2 as described in WO 2013/001087 or amylases having at least 85% identity thereto and having amylolytic activity. Suitable amylases include those having at least 85% identity compared to SEQ ID NO:2 and/or comprising a deletion of positions 181+182, or 182+183, or 183+184, which have amylolytic activity. Suitable amylases include those having at least 85% identity compared to SEQ ID NO:2 and/or comprising a deletion of positions 181+182, or 182+183, or 183+184, which comprise one or two or more modifications in any of positions corresponding to W140, W159, W167, Q169, W189, E194, N260, F262, W284, F289, G304, G305, R320, W347, W439, W469, G476 and G477 and have amylolytic activity.

Amylases also include hybrid α-amylases of the above mentioned amylases as for example as described in WO 2006/066594.

Commercially available amylase enzymes include: Amplify®, Duramyl™, Termamyl™, Fungamyl™, Stainzyme™, Stainzyme Plus™, Natalase™, Liquozyme X and BAN™ (from Novozymes A/S), and Rapidase™, Purastar™, Powerase™, Effectenz™ (M100 from DuPont), Preferenz™ (S1000, S110 and F1000; from DuPont), PrimaGreen™ (ALL; DuPont), Optisize™ (DuPont).

In one embodiment, the enzyme is a Termamyl-like amylase. In the present context, the term "Termamyl-like enzyme" is intended to indicate an α-amylase, which, at the amino acid level, has a sequence identity of at least 60% to the *B. licheniformis* α-amylase described in WO 96/23874. In an embodiment, the Termamyl-like α-amylase displays at least 70%, 75%, 80%, 85%, 90%, 95%, 97%, 99% identity to the *B. licheniformis* α-amylase described in WO 96/23874.

Another α-amylase herein is Natalase or a variant thereof as described in WO 95/26397, WO 99/19467 and WO 01/66712.

Lipase

"Lipase", "lipolytic enzyme", "lipid esterase", all refer to an enzyme of EC class 3.1.1 ("carboxylic ester hydrolase"). Lipases (E.C. 3.1.1.3, Triacylglycerol lipase) may hydrolyze triglycerides to more hydrophilic mono- and diglycerides, free fatty acids, and glycerol. Lipase enzymes usually includes also enzymes which are active on substrates different from triglycerides or cleave specific fatty acids, such as Phospholipase A (E.C. 3.1.1.4), Galactolipase (E.C. 3.1.1.26), cutinase (EC 3.1.1.74), and enzymes having sterol esterase activity (EC 3.1.1.13) and/or wax-ester hydrolase activity (EC 3.1.1.50).

Many lipase enzymes have been described in the prior art, including, but not being limited to: WO 00/032758, WO 03/089620, WO 2005/032496, WO 2005/086900, WO 2006/00976, WO 2006/031699, WO 2008/036863, WO 2011/046812, and WO 2014/059360.

Cellulase

"Cellulases", "cellulase enzymes" or "cellulolytic enzymes" are enzymes involved in the hydrolysis of cellulose. Three major types of cellulases are known, namely endo-beta-1,4-glucanase (endo-1,4-P-D-glucan 4-glucanohydrolase, E.C. 3.2.1.4; hydrolyzing β-1,4-glucosidic bonds in cellulose), cellobiohydrolase (1,4-P-D-glucan cellobiohydrolase, EC 3.2.1.91), and beta-glucosidase (EC 3.2.1.21).

Cellulase enzymes have been described in patents and published patent applications including, but not limited to: WO 97/025417, WO 98/024799, WO 03/068910, WO 2005/003319, and WO 2009/020459.

Commercially available cellulase enzymes include Celluzyme™, Endolase™, Carezyme™, Cellusoft™, Renozyme™, Celluclean™ (from Novozymes A/S), Ecostone™, Biotouch™ Econase™, Ecopulp™ (from AB Enzymes Finland), Clazinase™, and Puradax HA™ Genencor detergent cellulase L, IndiAge™ Neutra (from Genencor International Inc./DuPont), Revitalenz™ (2000 from DuPont), Primafast™ (DuPont) and KAC-500™ (from Kao Corporation).

Cellulases used in the methods according to the invention have "cellulolytic activity" or "cellulase activity". Assays for measurement of cellulolytic activity are known to those skilled in the art. For example, cellulolytic activity may be determined by virtue of the fact that cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

Mannanase

Mannase (E.C. 3.2.1.78) enzymes hydrolyse internal β-1,4 bonds in mannose polymers. "Mannanase" may be an alkaline mannanase of Family 5 or 26. Mannanase enzymes are known to be derived from wild-type from *Bacillus* or *Humicola*, particularly *B. agaradhaerens, B. licheniformis, B. halodurans, B. clausii,* or *H. insolens*. Suitable mannanases are described in WO 99/064619.

Commercially available mannanase enzymes include, but are not limited to, Mannaway® (Novozymes AIS).

Pectate Lyase

Pectate lyase (E.C. 4.2.2.2) enzymes catalyze eliminative cleavage of (1->4)-alpha-D-galacturonan to give oligosaccharides with 4-deoxy-alpha-D-galact-4-enuronosyl groups at their non-reducing ends.

Pectate lyase enzymes have been described in patents and published patent applications including, but not limited to: WO 2004/090099. Pectate lyases are known to be derived from *Bacillus*, particularly *B. licheniformis* or *B. agaradhaerens*, or a variant derived of any of these, e.g. as described in U.S. Pat. No. 6,124,127, WO 99/027083, WO 99/027084, WO 2002/006442, WO 02/092741, WO 03/095638.

Commercially available pectate lyase enzymes include: Xpect™, Pectawash™ and Pectaway™ (Novozymes A/S); PrimaGreen™, EcoScour (DuPont).

Nuclease

Nuclease (EC 3.1.21.1), also known as Deoxyribonuclease I, or Dnase, performs endonucleolytic cleavage to 5'-phosphodinucleotide and 5'-phosphooligonucleotide end-products.

Nuclease enzymes have been described in patents and published patent applications including, but not limited to: U.S. Pat. No. 3,451,935, GB 1300596, DE 10304331, WO 2015/155350, WO 2015/155351, WO 2015/166075, WO 2015/181287, and WO 2015/181286.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

After aligning the two sequences, in a second step, an identity value shall be determined from the alignment. Therefore, according to the present invention the following calculation of percent-identity applies:

%-identity=(identical residues/length of the alignment region which is showing the respective sequence of this invention over its complete length)*100. Thus sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity".

For calculating the percent identity of two DNA sequences the same applies as for the calculation of percent identity of two amino acid sequences with some specifications. For DNA sequences encoding for a protein the pairwise alignment shall be made over the complete length of the coding region from start to stop codon excluding introns. For non-protein-coding DNA sequences the pairwise alignment shall be made over the complete length of the sequence of this invention, so the complete sequence of this invention is compared to another sequence, or regions out of another sequence. Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

Protein Expression

There is no limitation on the origin of the protein of interest of the invention. Thus, the term protein of interest includes not only natural or wild-type proteins, but also any mutant variants, fragments, etc. of the protein of interest, as well as synthetic protein. Such genetically engineered proteins can be prepared as is generally known in the art, e.g., by site-directed mutagenesis, by PCR (using a PCR fragment containing the desired mutation as one of the primers in the PCR reactions), or by random mutagenesis.

The microorganism can comprise the gene encoding the protein of interest (i.e., gene of interest) endogenously or the gene of interest can be heterologous to the microbial cell. Preferably, the gene encoding the protein of interest is heterologous to the host cell.

The desired protein may be secreted into the liquid fraction of the fermentation broth or may remain inside the microbial cells. Preferably, the fermentation product is secreted by the microorganism into the fermentation broth. Secretion of the protein of interest into the fermentation medium allows for separation of the protein of interest from the fermentation broth. For secretion of the protein of interest into the fermentation medium the nucleic acid construct used for expressing the protein of interest comprises a polynucleotide encoding for a signal peptide that directs secretion of the protein of interest into the fermentation medium. Various signal peptides are known in the art. Preferred signal peptides are selected from the group consisting of the signal peptide of the AprE protein from *Bacillus subtilis* or the signal peptide from the YvcE protein from *Bacillus subitilis*.

Specific Embodiments

The following shows a list of specific embodiments of the invention:

In one embodiment, the present invention relates to a method of recovering a protein of interest from a fermentation broth comprising the steps of a) adding $CaCl_2$ to the fermentation broth or a fraction thereof comprising the protein of interest, and b) adjusting the pH of the fermentation broth to more than pH 11, and c) separating the protein of interest from impurities and/or biomass.

In one embodiment, the present invention relates to a method of recovering a protein of interest from a fermentation broth comprising the steps of a) adding $MgCl_2$ to the fermentation broth or a fraction thereof comprising the protein of interest, and b) adjusting the pH of the fermentation broth to more than pH 11, and c) separating the protein of interest from impurities and/or biomass.

In one embodiment, the present invention relates to a method of recovering a protease from a fermentation broth comprising the steps of
  a) adding a salt of a divalent cation to the fermentation broth or a fraction thereof comprising the protease, and
  b) adjusting the pH of the fermentation broth to more than pH 11, and
  c) separating the protease from impurities and/or biomass.

In one embodiment, the present invention relates to a method of recovering an amylase from a fermentation broth comprising the steps of
  a) adding a salt of a divalent cation to the fermentation broth or a fraction thereof comprising the amylase, and
  b) adjusting the pH of the fermentation broth to more than pH 11, and
  c) separating the amylase from impurities and/or biomass.

In one embodiment, the present invention relates to a method of recovering an α-amylase from a fermentation broth comprising the steps of
  a) adding a salt of a divalent cation to the fermentation broth or a fraction thereof comprising the α-amylase, and
  b) adjusting the pH of the fermentation broth to more than pH 11, and
  c) separating the α-amylase any impurities and/or biomass.

In one embodiment, the present invention relates to a method of recovering an α-amylase from a fermentation broth or a fraction thereof comprising the steps of
  a) adding a salt of a divalent cation to the fermentation broth or a fraction thereof comprising the protein of interest, and
  b) adjusting the pH of the fermentation broth or a fraction thereof to more than pH 11, and
  c) separating the protein of interest from impurities and/or biomass,
  wherein the fermentation broth or the fraction thereof prior to the addition of the divalent cation comprises phosphate, preferably, wherein the phosphate in the fermentation broth or the fraction thereof does not exceed 10 mmol after the addition of the salt of the divalent cation.

In one embodiment, the present invention relates to a method of recovering a protein of interest from a fermentation broth comprising the steps of
  a) adding a salt of a divalent cation to the fermentation broth or a fraction thereof comprising the protein of interest, and
  b) adjusting the pH of the fermentation broth to pH 11.5, and
  c) separating the protein of interest from impurities and/or biomass.

In one embodiment, the present invention relates to a method of recovering a protein of interest from a fermentation broth comprising the steps of
  a) adding a salt of a divalent cation to the fermentation broth or a fraction thereof comprising the protein of interest, and
  b) adjusting the pH of the fermentation broth to pH 12, and
  c) separating the protein of interest from impurities and/or biomass.

In one embodiment, the present invention relates to a method of recovering a protein of interest from a fermentation broth comprising the steps of
  a) adding a salt of a divalent cation to the fermentation broth or a fraction thereof comprising the protein of interest, and
  b) adjusting the pH of the fermentation broth to pH 12.5, and
  c) separating the protein of interest from impurities and/or biomass.

In one embodiment, the present invention relates to a method of recovering a protease from a fermentation broth comprising the steps of
  a) adding $CaCl_2$ to the fermentation broth or a fraction thereof comprising the protease, and
  b) adjusting the pH of the fermentation broth to more than pH 11, and
  c) separating the protease from impurities and/or biomass.

In one embodiment, the present invention relates to a method of recovering an amylase from a fermentation broth comprising the steps of
  a) adding $CaCl_2$ to the fermentation broth or a fraction thereof comprising the amylase, and
  b) adjusting the pH of the fermentation broth to more than pH 11, and
  c) separating the amylase from impurities and/or biomass.

In one embodiment, the present invention relates to a method of recovering an α-amylase from a fermentation broth comprising the steps of
  a) adding $CaCl_2$ to the fermentation broth or a fraction thereof comprising the α-amylase, and
  b) adjusting the pH of the fermentation broth to more than pH 11, and
  c) separating the α-amylase from impurities and/or biomass.

In one embodiment, the present invention relates to a method of recovering a protease from a fermentation broth comprising the steps of
  a) adding $MgCl_2$ to the fermentation broth or a fraction thereof comprising the protease, and
  b) adjusting the pH of the fermentation broth to more than pH 11, and
  c) separating the protease from impurities and/or biomass.

In one embodiment, the present invention relates to a method of recovering an amylase from a fermentation broth comprising the steps of
  a) adding $MgCl_2$ to the fermentation broth or a fraction thereof comprising the amylase, and
  b) adjusting the pH of the fermentation broth to more than pH 11, and
  c) separating the amylase from impurities and/or biomass.

In one embodiment, the present invention relates to a method of recovering an α-amylase from a fermentation broth comprising the steps of
  a) adding $MgCl_2$ to the fermentation broth or a fraction thereof comprising the α-amylase, and
  b) adjusting the pH of the fermentation broth to more than pH 11, and
  c) separating the α-amylase from impurities and/or biomass.

In one embodiment, the present invention relates to a method of recovering a protein of interest from a fermentation broth comprising the steps of
  a) adding $CaCl_2$ to the fermentation broth or a fraction thereof comprising the protein of interest, and
  b) adjusting the pH of the fermentation broth to pH 11.5, and c) separating the protein of interest from impurities and/or biomass.

In one embodiment, the present invention relates to a method of recovering a protein of interest from a fermentation broth comprising the steps of
  a) adding $CaCl_2$ to the fermentation broth or a fraction thereof comprising the protein of interest, and
  b) adjusting the pH of the fermentation broth to pH 12, and
  c) separating the protein of interest from impurities and/or biomass.

In one embodiment, the present invention relates to a method of recovering a protein of interest from a fermentation broth comprising the steps of
  a) adding $CaCl_2$ to the fermentation broth or a fraction thereof comprising the protein of interest, and
  b) adjusting the pH of the fermentation broth to pH 12.5, and
  c) separating the protein of interest from impurities and/or biomass.

In one embodiment, the present invention relates to a method of recovering a protein of interest from a fermentation broth comprising the steps of
  a) adding $MgCl_2$ to the fermentation broth or a fraction thereof comprising the protein of interest, and
  b) adjusting the pH of the fermentation broth to pH 11.5, and
  c) separating the protein of interest from impurities and/or biomass.

In one embodiment, the present invention relates to a method of recovering a protein of interest from a fermentation broth comprising the steps of
  a) adding $MgCl_2$ to the fermentation broth or a fraction thereof comprising the protein of interest, and
  b) adjusting the pH of the fermentation broth to pH 12, and
  c) separating the protein of interest from impurities and/or biomass.

In one embodiment, the present invention relates to a method of recovering a protein of interest from a fermentation broth comprising the steps of
  a) adding $MgCl_2$ to the fermentation broth or a fraction thereof comprising the protein of interest, and
  b) adjusting the pH of the fermentation broth to pH 12.5, and
  c) separating the protein of interest from impurities and/or biomass.

In one embodiment, the present invention relates to a method of recovering a protease from a fermentation broth comprising the steps of
  a) adding a salt of a divalent cation to the fermentation broth or a fraction thereof comprising the protease, and
  b) adjusting the pH of the fermentation broth to pH 11.5, and
  c) separating the protease from impurities and/or biomass.

In one embodiment, the present invention relates to a method of recovering a protease from a fermentation broth comprising the steps of
  a) adding a salt of a divalent cation to the fermentation broth or a fraction thereof comprising the protease, and
  b) adjusting the pH of the fermentation broth to pH 12, and
  c) separating the protease from impurities and/or biomass.

In one embodiment, the present invention relates to a method of recovering a protease from a fermentation broth comprising the steps of
  a) adding a salt of a divalent cation to the fermentation broth or a fraction thereof comprising the protease, and
  b) adjusting the pH of the fermentation broth to pH 12.5, and
  c) separating the protease from impurities and/or biomass.

In one embodiment, the present invention relates to a method of recovering a protease from a fermentation broth comprising the steps of
  a) adding $CaCl_2$ to the fermentation broth or a fraction thereof comprising the protease, and
  b) adjusting the pH of the fermentation broth to pH 11.5, and
  c) separating the protease from impurities and/or biomass.

In one embodiment, the present invention relates to a method of recovering a protease from a fermentation broth comprising the steps of
  a) adding $CaCl_2$ to the fermentation broth or a fraction thereof comprising the protease, and
  b) adjusting the pH of the fermentation broth to pH 12, and
  c) separating the protease from impurities and/or biomass.

In one embodiment, the present invention relates to a method of recovering a protease from a fermentation broth comprising the steps of
  a) adding $CaCl_2$ to the fermentation broth or a fraction thereof comprising the protease, and
  b) adjusting the pH of the fermentation broth to pH 12.5, and
  c) separating the protease from impurities and/or biomass.

In one embodiment, the present invention relates to a method of recovering a protease from a fermentation broth comprising the steps of
  a) adding $MgCl_2$ to the fermentation broth or a fraction thereof comprising the protease, and
  b) adjusting the pH of the fermentation broth to pH 11.5, and
  c) separating the protease from impurities and/or biomass.

In one embodiment, the present invention relates to a method of recovering a protease from a fermentation broth comprising the steps of
  a) adding $MgCl_2$ to the fermentation broth or a fraction thereof comprising the protease, and
  b) adjusting the pH of the fermentation broth to pH 12, and
  c) separating the protease from impurities and/or biomass.

In one embodiment, the present invention relates to a method of recovering a protease from a fermentation broth comprising the steps of
  a) adding $MgCl_2$ to the fermentation broth or a fraction thereof comprising the protease, and
  b) adjusting the pH of the fermentation broth to pH 12.5, and
  c) separating the protease from impurities and/or biomass.

In one embodiment, the present invention relates to a method of recovering an amylase from a fermentation broth comprising the steps of
  a) adding a salt of a divalent cation to the fermentation broth or a fraction thereof comprising the amylase, and
  b) adjusting the pH of the fermentation broth to pH 11.5, and
  c) separating the amylase from impurities and/or biomass.

In one embodiment, the present invention relates to a method of recovering an amylase from a fermentation broth comprising the steps of
  a) adding a salt of a divalent cation to the fermentation broth or a fraction thereof comprising the amylase, and b) adjusting the pH of the fermentation broth to pH 12, and c) separating the amylase from impurities and/or biomass.

In one embodiment, the present invention relates to a method of recovering an amylase from a fermentation broth comprising the steps of a) adding a salt of a divalent cation to the fermentation broth or a fraction thereof comprising the amylase, and b) adjusting the pH of the fermentation broth to pH 12.5, and c) separating the amylase from impurities and/or biomass.

In one embodiment, the present invention relates to a method of recovering an amylase from a fermentation broth comprising the steps of a) adding $CaCl_2$ to the fermentation broth or a fraction thereof comprising the amylase, and b) adjusting the pH of the fermentation broth to pH 11.5, and c) separating the amylase from impurities and/or biomass.

In one embodiment, the present invention relates to a method of recovering an amylase from a fermentation broth comprising the steps of a) adding $CaCl_2$ to the fermentation broth or a fraction thereof comprising the amylase, and b) adjusting the pH of the fermentation broth to pH 12, and c) separating the amylase from impurities and/or biomass.

In one embodiment, the present invention relates to a method of recovering an amylase from a fermentation broth comprising the steps of a) adding $CaCl_2$ to the fermentation broth or a fraction thereof comprising the amylase, and b) adjusting the pH of the fermentation broth to pH 12.5, and c) separating the amylase from impurities and/or biomass.

In one embodiment, the present invention relates to a method of recovering an amylase from a fermentation broth comprising the steps of a) adding $MgCl_2$ to the fermentation broth or a fraction thereof comprising the amylase, and b) adjusting the pH of the fermentation broth to pH 11.5, and c) separating the amylase from impurities and/or biomass.

In one embodiment, the present invention relates to a method of recovering an amylase from a fermentation broth comprising the steps of a) adding $MgCl_2$ to the fermentation broth or a fraction thereof comprising the amylase, and b) adjusting the pH of the fermentation broth to pH 12, and c) separating the amylase from impurities and/or biomass.

In one embodiment, the present invention relates to a method of recovering an amylase from a fermentation broth comprising the steps of a) adding $MgCl_2$ to the fermentation broth or a fraction thereof comprising the amylase, and b) adjusting the pH of the fermentation broth to pH 12.5, and c) separating the amylase from impurities and/or biomass.

In one embodiment, the present invention relates to a method of recovering an α-amylase from a fermentation broth comprising the steps of a) adding a salt of a divalent cation to the fermentation broth or a fraction thereof comprising the α-amylase, and b) adjusting the pH of the fermentation broth to pH 11.5, and c) separating the α-amylase from impurities and/or biomass.

In one embodiment, the present invention relates to a method of recovering an α-amylase from a fermentation broth comprising the steps of a) adding a salt of a divalent cation to the fermentation broth or a fraction thereof comprising the α-amylase, and b) adjusting the pH of the fermentation broth to pH 12, and c) separating the α-amylase from impurities and/or biomass.

In one embodiment, the present invention relates to a method of recovering an α-amylase from a fermentation broth comprising the steps of a) adding a salt of a divalent cation to the fermentation broth or a fraction thereof comprising the α-amylase, and b) adjusting the pH of the fermentation broth to pH 12.5, and c) separating the α-amylase from impurities and/or biomass.

In one embodiment, the present invention relates to a method of recovering an α-amylase from a fermentation broth comprising the steps of a) adding $CaCl_2$ to the fermentation broth or a fraction thereof comprising the α-amylase, and b) adjusting the pH of the fermentation broth to pH 11.5, and c) separating the α-amylase from ay impurities and/or biomass.

In one embodiment, the present invention relates to a method of recovering an α-amylase from a fermentation broth comprising the steps of a) adding $CaCl_2$ to the fermentation broth or a fraction thereof comprising the α-amylase, and b) adjusting the pH of the fermentation broth to pH 12, and c) separating the α-amylase from impurities and/or biomass.

In one embodiment, the present invention relates to a method of recovering an α-amylase from a fermentation broth comprising the steps of a) adding $CaCl_2$ to the fermentation broth or a fraction thereof comprising the α-amylase, and b) adjusting the pH of the fermentation broth to pH 12.5, and c) separating the α-amylase from impurities and/or biomass.

In one embodiment, the present invention relates to a method of recovering an α-amylase from a fermentation broth comprising the steps of a) adding $MgCl_2$ to the fermentation broth or a fraction thereof comprising the α-amylase, and b) adjusting the pH of the fermentation broth to pH 11.5, and c) separating the α-amylase from impurities and/or biomass.

In one embodiment, the present invention relates to a method of recovering an α-amylase from a fermentation broth comprising the steps of a) adding $MgCl_2$ to the fermentation broth or a fraction thereof comprising the α-amylase, and b) adjusting the pH of the fermentation broth to pH 12, and c) separating the α-amylase from impurities and/or biomass.

In one embodiment, the present invention relates to a method of recovering an α-amylase from a fermentation broth comprising the steps of
 a) adding MgCl$_2$ to the fermentation broth or a fraction thereof comprising the α-amylase, and
 b) adjusting the pH of the fermentation broth to pH 12.5, and
 c) separating the α-amylase from impurities and/or biomass.

The invention is further illustrated in the following examples which are not intended to be in any way limiting to the scope of the invention as claimed.

EXAMPLES

The following examples only serve to illustrate the invention. The numerous possible variations that are obvious to a person skilled in the art also fall within the scope of the invention.

Unless otherwise stated the following experiments have been performed by applying standard equipment, methods, chemicals, and biochemicals as used in genetic engineering and fermentative production of chemical compounds by cultivation of microorganisms. See also Sambrook et al. (Molecular Cloning: A Laboratory Manual. 2nd edition, Cold Spring Harbor Laboratory, Cold Spring Harbor Laboratory Press, Cold Spring Harbor, NY, 1989) and Chmiel et al. (Bioprocesstechnik 1. Einführung in die Bioverfahrenstechnik, Gustav Fischer Verlag, Stuttgart, 1991).

The fermentation broths for the examples below (Examples 1-3) were obtained by culturing *Bacillus licheniformis* cells comprising a gene coding for an amylase which is a variant of the SP722 amylase disclosed in WO 96/23873. *Bacillus licheniformis* cells were cultivated in a fermentation process using a chemically defined fermentation medium providing the components listed in Table 1 and Table 2.

TABLE 1

Macroelements provided during the course of the fermentation process

| Compound | Formula | Concentration [g/L initial volume] |
|---|---|---|
| Citric acid | C$_6$H$_8$O$_7$ | 3.0 |
| Calcium sulfate | CaSO$_4$ | 0.7 |
| Monopotassium phosphate | KH$_2$PO$_4$ | 25 |
| Magnesium sulfate | MgSO$_4$*7H$_2$O | 4.8 |
| Sodium hydroxide | NaOH | 4.0 |
| Ammonia | NH$_3$ | 1.3 |

TABLE 2

Trace elements provided during the course of the fermentation process

| Trace element | Symbol | Concentration [mM] |
|---|---|---|
| Manganese | Mn | 24 |
| Zinc | Zn | 17 |
| Copper | Cu | 32 |
| Cobalt | Co | 1 |
| Nickel | Ni | 2 |
| Molybdenum | Mo | 0.2 |
| Iron | Fe | 38 |

A solution containing 50% glucose was used as feed solution. pH was adjusted during fermentation using ammonia. At the desired product titer the fermentation was terminated, and the product amylase was present in both soluble and crystalline form as confirmed by visual inspection using a microscope. At the end of fermentation, the phosphate concentration was about 3 g/L.

Example 1

The following example shows that a pH level of more than 11.0 is needed to dissolve (solubilize) a substantial fraction of the present amylase crystals in the fermentation broth. The fermentation broth was adjusted to pH levels 11.0, 11.5 and 12.0 by adding diluted (10% (w/v)) NaOH solution under stirring. As soon as the desired pH was reached, optical density samples of the 0 min time point were taken, and the supernatant was further incubated up to 120 min under stirring. Further samples were taken at several time points during the incubation period. To determine the optical density at 700 nm (OD700), the samples were diluted 1:100 with water and then measured in a photometer at 700 nm.

The OD700 values decreased during the first 15 min of incubation to a plateau value (FIG. 1). The decrease in OD700 reflects crystal dissolution. FIG. 1 shows that the degree of crystal dissolution (solubilization) depends on the pH level of the solution with higher pH levels resulting in better crystal dissolution. Importantly, a pH level of more than 11.0 is needed to dissolve an acceptable fraction of the amylase crystals for further recovery and purification operations.

Example 2

The following example shows that without prior addition of CaCl$_2$ substantial loss of enzyme activity in the soluble fraction occurs at pH levels above 11.

The fermentation broth was centrifuged in a laboratory centrifuge at 10000 g for 10 min. The supernatant was adjusted to pH levels 11.0, 11.5 and 12.0 by adding diluted (10% (w/v)) NaOH solution under stirring. As soon as the desired pH was reached, enzyme activity samples of the 0 min time point were taken, and the supernatant was further incubated up to 120 min under stirring. Further samples were taken at several time points during the incubation period. To determine the remaining enzyme activity, the samples were diluted directly into analysis buffer (50% MPG, MOPS, pH=7), centrifuged and the supernatant was analyzed using an amylase activity assay (Lorentz K. et al. (2000), *Clin. Chem.*, 46/5: 644 — 649).

Figure 2:
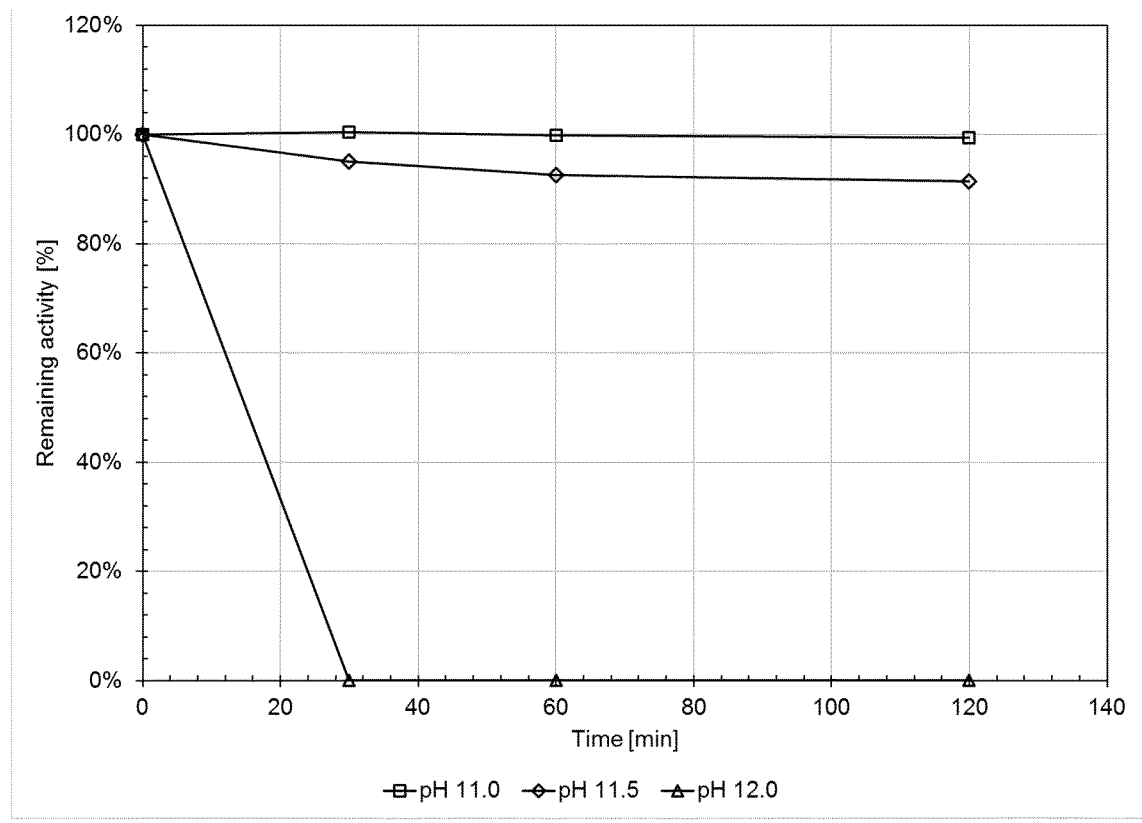
FIG. 2: Amylase activity dependent on the pH of the supernatant.

In FIG. 2 the remaining enzyme activity of the amylase containing supernatant relative to the 0 min value of every sample is shown. The pH 11 sample showed a decrease of activity of 1 percentage points over 120 min. The pH 11.5 sample showed a decrease of activity of 9 percentage points over 120 min, wherein the highest decrease was observed in the first 30 min. The pH 12.0 sample lost complete activity in the first 30 min.

Example 3

The following example shows that addition of CaCl$_2$ prior to adjusting the pH level above 11.0 prevents substantial loss of enzyme activity in the soluble fraction.

The fermentation broth was centrifuged in a laboratory centrifuge at 10000 g for 10 min. Prior to adjusting the pH, 7.5 g/L CaCl$_2$ was added to the supernatant under stirring. The supernatant was then adjusted to pH levels 11.0, 11.5 and 12.0 by adding diluted (10% (w/v)) NaOH solution under stirring. As soon as the desired pH was reached, activity samples of the 0 min time point were taken, and the supernatant was further incubated up to 120 min under stirring. Further samples were taken at several time points during the incubation period. To determine the remaining enzyme activity, the samples were diluted directly into analysis buffer (50% MPG, MOPS, pH=7), centrifuged and the supernatant was analyzed using an amylase activity assay (Lorentz K. et al. (2000), *Clin. Chem.*, 46/5: 644 — 649).

Figure 3:
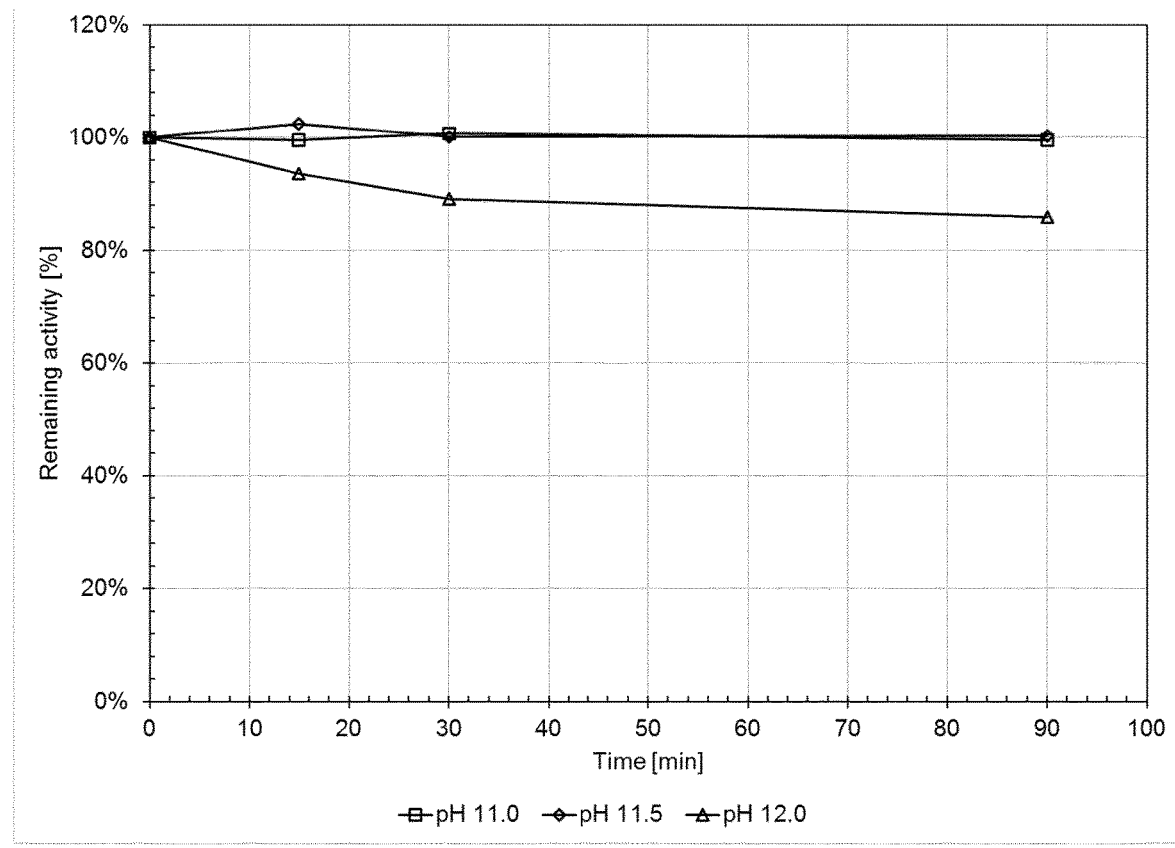
FIG. 3: Amylase activity dependent on the pH of the supernatant in the presence of 7.5 g/l calcium chloride.

In FIG. 3 the remaining enzyme activity of the amylase containing supernatant relative to the 0 min value of every sample is shown. The pH 11.0 and pH 11.5 samples showed almost no activity decrease over 90 min. The pH 12.0 sample lost about 14 percentage points of activity over 90 min. In comparison to the results in Example 2 it shows that the addition of $CaCl_2$ prevents enzyme activity loss at pH 11.5 almost completely and reduced enzyme activity loss at pH 12.0 significantly.

The invention claimed is:

1. A method of recovering a protein of interest from a fermentation broth comprising:
    a) adding a salt of a divalent cation to the fermentation broth or a fraction thereof comprising the protein of interest,
    b) adjusting the pH of the fermentation broth to more than pH 11 to at most pH 12.5, and
    c) separating the protein of interest from impurities and/or biomass,
    wherein the protein of interest is an amylase, and wherein the fermentation broth or the fraction thereof prior to the addition of the divalent cation comprises phosphate, wherein the phosphate in the fermentation broth or the fraction of does not exceed a concentration of 10 mmol after the addition of the salt of the divalent cation.

2. The method according to claim 1, wherein the divalent cation is selected from the group consisting of $Ca^{2+}$, $Mg^{2+}$, $Ba^{2+}$, $Pb^{2+}$, $Fe^{2+}$, $Zn^{2+}$, $Ni^{2+}$, $Cu^{2+}$, $Mn^{2+}$, $Sr^{2+}$, $Co^{2+}$ and $Be^{2+}$.

3. The method according to claim 2, wherein the salt of the divalent cation is the chloride, nitrate, formate, acetate, phosphate or sulfate salt of the divalent cation.

4. The method according to claim 1, wherein step a) is performed before step b).

5. The method according to claim 1, wherein the fraction of the fermentation broth is the supernatant obtained by centrifugation of the fermentation broth or wherein the fraction of the fermentation broth is the filtrate obtained by filtration of the fermentation broth.

6. The method according to claim 1, wherein the pH is adjusted by adding NaOH.

7. The method according to claim 1, wherein the method further comprises prior to step a) and/or b) the fermentation of a microorganism.

8. The method of claim 7, wherein the protein of interest is secreted by the microorganism into the fermentation broth.

9. The method according to claim 7, wherein the microorganism is a bacterium or a fungal cell.

10. The method according to claim 1, wherein the salt of the divalent cation is added to the fermentation broth to obtain a final concentration of 0.01-5% (w/v) of the salt of the divalent cation in the broth.

11. The method according to claim 1, further comprising a step (d) of preparing a formulation containing the protein of interest.

12. A method of stabilizing a protein of interest in a fermentation broth or a fraction thereof, said method comprising:
    a) adding a salt of a divalent cation to the fermentation broth comprising the protein of interest, and
    b) adjusting the pH of the fermentation broth to a pH of more than 11 to at most pH 12.5,
    wherein the protein of interest is an amylase, and wherein the fermentation broth or the fraction thereof prior to the addition of the divalent cation comprises phosphate, wherein the phosphate in the fermentation broth or the fraction of does not exceed a concentration of 10 mmol after the addition of the salt of the divalent cation.

13. The method according to claim 9 wherein the microorganism is a bacterium.

* * * * *